(12) United States Patent
Owen et al.

(10) Patent No.: US 10,253,256 B2
(45) Date of Patent: Apr. 9, 2019

(54) USE OF SULFUR AND SELENIUM COMPOUNDS AS PRECURSORS TO NANOSTRUCTURED MATERIALS

(71) Applicant: THE TRUSTEES OF COLUMBIA UNIVERSITY IN THE CITY OF NEW YORK, New York, NY (US)

(72) Inventors: Jonathan S. Owen, New York, NY (US); Mark P. Hendricks, Richland, WA (US); Michael P. Campos, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 203 days.

(21) Appl. No.: 15/024,550

(22) PCT Filed: Sep. 26, 2014

(86) PCT No.: PCT/US2014/057740
§ 371 (c)(1),
(2) Date: Mar. 24, 2016

(87) PCT Pub. No.: WO2015/048460
PCT Pub. Date: Apr. 2, 2015

(65) Prior Publication Data
US 2016/0237345 A1 Aug. 18, 2016

Related U.S. Application Data

(60) Provisional application No. 61/883,544, filed on Sep. 27, 2013, provisional application No. 61/953,325, (Continued)

(51) Int. Cl.
*C09K 11/88* (2006.01)
*C09K 11/56* (2006.01)
(Continued)

(52) U.S. Cl.
CPC .............. *C09K 11/883* (2013.01); *B05D 1/18* (2013.01); *C01B 19/007* (2013.01); *C01B 19/04* (2013.01);
(Continued)

(58) Field of Classification Search
CPC ..... C09K 11/02; C09K 11/565; C09K 11/582; C09K 11/661; C09K 11/883; C01G 11/02;
(Continued)

(56) References Cited

U.S. PATENT DOCUMENTS

2005/0254528 A1 11/2005 Galun et al.
2006/0234417 A1* 10/2006 Isobe ................... C09K 11/574
438/99
(Continued)

FOREIGN PATENT DOCUMENTS

CN 1645559 A 7/2005
EP 2669409 A1 12/2013
(Continued)

OTHER PUBLICATIONS

Abe et al., "Tuning the Postfocused Size of Colloidal Nanocrystals by the Reaction Rate: From Theory to Application", ACS Nano, Jan. 24, 2012, vol. 6, No. 1, 42-53.
(Continued)

*Primary Examiner* — Matthew E. Hoban
*Assistant Examiner* — Lynne Edmondson
(74) *Attorney, Agent, or Firm* — Baker & Hostetler LLP

(57) ABSTRACT

The presently disclosed subject matter provides processes for preparing nanocrystals, including processes for preparing core-shell nanocrystals. The presently disclosed subject matter also provides sulfur and selenium compounds as precursors to nanostructured materials. The presently dis-
(Continued)

closed subject matter also provides nanocrystals having a particular particle size distribution.

30 Claims, 13 Drawing Sheets

Related U.S. Application Data filed on Mar. 14, 2014, provisional application No. 62/009,093, filed on Jun. 6, 2014, provisional application No. 62/023,155, filed on Jul. 10, 2014.

(51) Int. Cl.

| | | |
|---|---|---|
| C09K 11/58 | (2006.01) | |
| C09K 11/66 | (2006.01) | |
| C09K 11/02 | (2006.01) | |
| C01B 19/04 | (2006.01) | |
| C01G 21/21 | (2006.01) | |
| C01G 3/12 | (2006.01) | |
| C01G 11/02 | (2006.01) | |
| C07C 335/16 | (2006.01) | |
| C07F 7/00 | (2006.01) | |
| C07C 335/08 | (2006.01) | |
| C07C 391/00 | (2006.01) | |
| C07D 207/34 | (2006.01) | |
| C01B 19/00 | (2006.01) | |
| B05D 1/18 | (2006.01) | |
| B82Y 20/00 | (2011.01) | |
| B82Y 40/00 | (2011.01) | |

(52) U.S. Cl.
CPC ............... *C01G 3/12* (2013.01); *C01G 11/02* (2013.01); *C01G 21/21* (2013.01); *C07C 335/08* (2013.01); *C07C 335/16* (2013.01); *C07C 391/00* (2013.01); *C07D 207/34* (2013.01); *C07F 7/003* (2013.01); *C09K 11/02* (2013.01); *C09K 11/565* (2013.01); *C09K 11/582* (2013.01); *C09K 11/661* (2013.01); *B82Y 20/00* (2013.01); *B82Y 40/00* (2013.01); *C01P 2004/04* (2013.01); *C01P 2004/64* (2013.01); *C07C 2601/14* (2017.05); *Y10S 977/774* (2013.01); *Y10S 977/892* (2013.01); *Y10S 977/95* (2013.01)

(58) Field of Classification Search
CPC .......... C01G 21/21; C01G 3/12; C01B 19/04; C01P 2004/64
See application file for complete search history.

(56) References Cited

U.S. PATENT DOCUMENTS

| | | | |
|---|---|---|---|
| 2009/0289233 A1 | 11/2009 | Jang et al. | |
| 2010/0041017 A1* | 2/2010 | Tsukada | B82Y 15/00 435/5 |
| 2010/0261304 A1* | 10/2010 | Chang | C23C 18/06 438/72 |
| 2011/0001096 A1 | 1/2011 | Mokari et al. | |
| 2013/0032767 A1* | 2/2013 | Manna | 252/519.4 |
| 2014/0144500 A1* | 5/2014 | Cao | H01L 21/0237 136/256 |

FOREIGN PATENT DOCUMENTS

| | | |
|---|---|---|
| WO | WO 2010/118279 A1 | 10/2010 |
| WO | WO 2013/091114 A1 | 6/2013 |

OTHER PUBLICATIONS

Akhtar et al., "A Single-Source Precursor Route to Unusual PbSe Nanostructures by a Solution-Liquid-Solid Method", Journal of the American Chemical Society, Feb. 8, 2012, vol. 134, No. 5, 2485-2487.

Bruce et al., "Cadium(ii) complexes of N,N-diethyl-N'-benzoylthio(seleno) urea as single-source precursors for the preparation of CdS and CdSe nanoparticles", New Journal of Chemistry, Jun. 8, 2007, vol. 31, No. 9, p. 1647.

Martin et al., "Luminescent thin films by the chemical aerosol deposition technology (CADT)", Journal of Aerosol Science, Jan. 1, 1991, vol. 22, S435-S438.

Sreekumari et al., "Thermal decomposition of single source precursors and the shape evolution of CdS and CdSe nanocrystals", Journal of Materials Chemistry, Nov. 18, 2005, vol. 16, No. 5, 467-473.

Chen et al., "Compact high-quality CdSe/CdS core/shell nanocrystals with narrow emission linewidths and suppressed blinking", Nature Materials, May 2013, 12, 5, 445-451.

Moreels et al., "Composition and Size-Dependent Extinction Coefficient of Colloidal PbSe Quantum Dots", Chemistry of Materials, Nov. 15, 2007, 19, 25, 6101-6106.

Moreels et al., "Size-Dependent Optical Properties of Colloidal PbS Quantum Dots", ACS Nano, Sep. 25, 2009, 3, 10, 3023-3030.

Owen et al., "Precursor Conversion Kinetics and the Nucleation of Cadmium Selenide Nanocrystals", Journal of the American Chemical Society, Dec. 3, 2010, 132, 51, 18206-18213.

Zhang et al., "A Generic Method for Rational Scalable Synthesis of Monodisperse Metal Sulfide Nanocrystals", Nano Letters, Oct. 3, 2012, 12, 5856-5860.

* cited by examiner

|   | R₁ | R₂ | Temp. (°C) | $k_{rel}$ |
|---|---|---|---|---|
| 1 | Ph | Ph | 120 | 67 |
| 2a | p-CN-Ph | n-dodecyl | 120 | 9.4 |
| 2b | p-CF₃-Ph | n-dodecyl | 120 | 4.3 |
| 2c | p-Cl-Ph | n-dodecyl | 120 | 2.1 |
| 2d | Ph | n-dodecyl | 120 | 1.0 |
| 2e | p-Me-Ph | n-dodecyl | 120 | 0.77 |
| 2f | p-OMe-Ph | n-dodecyl | 120, 150 | 0.53 |
| 3 | t-butyl | n-dodecyl | 150 | 0.46 |
| 4 | isopropyl | n-dodecyl | 150 | 0.12 |
| 5 | cyclohexyl | n-dodecyl | 150 | 0.11 |
| 6 | n-hexyl | n-dodecyl | 150 | 0.047 |

X = CN, CF₃, Cl, H, Me, MeO
R = t-butyl, isopropyl, cyclohexyl, n-hexyl

→ SLOWER

Degree of substitution most important: 4° < 3° < 2°
Electronics matter: alkyl < phenyl
Sterics also matter: Me < $n$-Bu < $i$Pr < $t$-Bu

USE OF SULFUR AND SELENIUM COMPOUNDS AS PRECURSORS TO NANOSTRUCTURED MATERIALS

PRIORITY CLAIM

This application is a National Stage application filed under 35 U.S.C. 371 of International Application No. PCT/US2014/057740 filed Sep. 26, 2014, which claims priority under 35 U.S.C. § 119 to U.S. Provisional Application No. 61/883,544, filed Sep. 27, 2013; U.S. Provisional Application No. 61/953,325, filed Mar. 14, 2014; U.S. Provisional Application No. 62/009,093, filed Jun. 6, 2014; and to U.S. Provisional Application No. 62/023,155, filed Jul. 10, 2014. The contents of all of the preceding applications are hereby incorporated by reference in their entireties for any and all purposes.

STATEMENT OF GOVERNMENT SUPPORT

This invention was made with government support under grant 1151172 awarded by the National Science Foundation. The Government has certain rights in the invention.

BACKGROUND

The presently disclosed subject matter relates to processes for preparing nanocrystals, including processes for preparing core-shell nanocrystals.

Synthetic advances have improved understanding of quantum confined metal chalcogenide semiconductor nanocrystals, known as quantum dots (QD or QDs). Scalability of synthesis, control over nanocrystal size, control over distribution of nanocrystal size, and control of photoluminescence quantum yield have all improved in recent years. However, many of these synthetic advances have been achieved by empirical optimization because nanocrystal formation can be a complex process that is controlled by many interdependent variables. This difficulty can be made worse by a limited collection of chalcogen precursors, many of which are pyrophoric, toxic, difficult to purify, too reactive, or too unreactive. Such issues can limit synthetic reproducibility and create nanocrystals with ill-defined chemical compositions. Improved precursors are thus broadly important to nanocrystal science, both because they can provide access to materials with optimized optoelectronic properties and because they can increase understanding of crystallization mechanisms and nanocrystal structure.

One subclass of quantum confined metal chalcogenide nanocrystals is core-shell nanocrystals, which can be used as phosphors for lighting, given that their size and interfacial composition can be precisely controlled to optimize their luminescence wavelength linewidth, quantum yield and their photostability. To achieve the performance needed for certain on-chip lighting applications, these materials should withstand high operating temperatures (e.g., 150° C.) and intense illumination fluxes (e.g., 200 W/cm2) that can lead to multiexciton Auger recombination and photochemical degradation. High performance materials can have graded alloy compositions that serve two purposes: they reduce the multiexciton Auger recombination rates and minimize interfacial strain, thereby allowing the conformity and stability of shelling layers. However, the structure of high performance interfaces can be difficult to control.

Among classes of colloidal crystallizations, semiconductor quantum dots are thought to form via homogeneous nucleation and growth mechanisms proposed by La Mer, a three-phase mechanism shown in FIG. 1. Monomers (ME) are generated by a slow reaction between a metal salt ($MX_2$) and a chalcogen precursor ($ER_2$) that can limit subsequent crystallization (FIG. 2). FIG. 2 is a scheme presenting a generalized mechanism of precursor-limited homogeneous nucleation and growth of nanocrystals. The precursor conversion rate can play a role in the kinetics of nanocrystal nucleation and growth by determining the kinetics of monomer supply to the crystallization medium. The monomer supply rate during the nucleation phase can control the number of nanocrystals produced and therefore can be used to control the final size and size distribution.

Examples of sulfur precursors include phosphine sulfides ($R_3P=S$), bis-trimethylsilyl sulfide (($TMS)_2S$), and alkyldithiocarbamates. Hydrogen sulfide (HS), can also serve as a sulfur precursor. Hydrogen sulfide can be produced by heating elemental sulfur in alkane and/or amine solvents. For example, elemental sulfur can be reduced in the presence of alkylamines and 1-octadecene producing soluble sources of hydrogen sulfide, which can then be used to prepare metal sulfides.

$(TMS)_2S$ reacts rapidly with metal salts at temperatures near room temperature (about 20-25° C.), leading to reactions that can be complicated by the kinetics of injection. These complications can limit reaction scale and reproducibility. $R_3P=S$ derivatives can react sluggishly above 300° C. and produce low reaction yields. Reactions of elemental sulfur with alkanes and amines, which generate hydrogen sulfide, can be used at intermediate temperatures. However, reactions of elemental sulfur with alkanes and amines generally follow ill-defined radical pathways that can be difficult to control, can be sensitive to the presence of impurities, and can produce sulfur-containing byproducts that can have detrimental effects on nanocrystal properties and limit atom economy. These precursors can suffer from other drawbacks, such as being air-sensitive, producing toxic and noxious hydrogen sulfide, and producing unreliable results.

There are certain selenium-containing precursor compounds known in the art. Examples of selenium precursors include elemental selenium, selenium dioxide, trialkylphosphine selenides and diphenylphosphine selenide. Existing selenium precursors can suffer from many drawbacks similar to those associated with sulfur precursors, with additional complications arising from increased air sensitivity. Phosphine selenide precursor reactivity can be dominated by impurities, and pure phosphine selenide precursors can fail to react quantitatively to provide metal selenide nanocrystals. Reactions of elemental selenium or selenium dioxide with alkanes, alkenes, and/or amines can generate hydrogen selenide in situ, but they can follow poorly defined pathways and generate byproducts that are difficult to control. Such byproducts can reduce atom economy and lead to irreproducibility and impaired nanocrystal properties.

Scalability and reproducibility can be a challenge in preparation of core-shell nanoparticles. One route to core-shell nanoparticles is contacting a core nanocrystal with a mixture that contains a metal salt and a sulfur- or selenium-containing precursor compound, a "shelling" process that will build a metal sulfide or metal selenide shell around the core nanocrystal. However, certain precursor compounds have unpredictable kinetics, and can present challenges that are magnified as the scale of the synthetic batch is increased.

Nanocrystals under 4 nm can be difficult to synthesize with current methods, despite interest in their near-infrared absorption and luminescence arising from strong quantum confinement. Existing procedures can afford poor conversion.

Thus there remains a general need in the art for improved techniques relating to the synthesis of high performance semiconductor nanoparticles and quantum dots, including core-shell architectures.

SUMMARY

The disclosed subject matter provides techniques for using substituted sulfur and selenium compounds as precursors for metal sulfide and metal selenide nanocrystal synthesis. The disclosed subject matter also provides techniques for preparing nanocrystals, including processes for preparing core-shell nanocrystals. The disclosed subject matter also provides nanocrystals having a particular particle size distribution.

In one aspect of the disclosed subject matter, substituted thioureas are presented as a family of precursors for metal sulfide nanocrystal synthesis. Certain precursors can be synthesized by combining commercially available isothiocyanates with primary or secondary amines. The reaction of thioureas with metal carboxylate, phosphonate, and/or halide complexes can be used to synthesize nanocrystals, or to grow core-shell heterostructures. In certain embodiments, the reaction rate of the precursor can follow pseudo first-order decomposition kinetics that can depend on the substituents and reaction temperature.

In one aspect of the disclosed subject matter, binary metal sulfides are synthesized. According to another aspect, the techniques of the disclosed subject matter can be used to prepare di-, tri-, and tetrasubstituted selenoureas and related compounds. In exemplary embodiments, metal salts and selenoureas can be utilized to synthesize metal selenide nanocrystals or metal selenide shells for pre-existing nanocrystals. In other exemplary embodiments, metal salts and sulfur precursors can be utilized to synthesize metal sulfide nanocrystals or metal sulfide shells for pre-existing nanocrystals.

In a non-limiting embodiment of the presently disclosed subject matter, a process for preparing nanocrystals includes contacting a metal salt with a precursor compound. The precursor compound can be of the general formula:

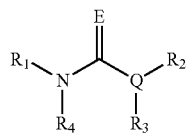

wherein E is S or Se; Q is N, O, S, Se, or P; $R_1$, $R_2$, $R_3$, and $R_4$ are independently selected from the group consisting of H, substituted or unsubstituted alkyl, substituted or unsubstituted alkenyl, substituted or unsubstituted cycloalkyl, substituted or unsubstituted cycloalkenyl, and substituted and unsubstituted aryl, or $R_3$ and $R_4$, taken together, form a ring, which can be substituted or unsubstituted; with the proviso that when Q is O, S, or Se, $R_2$ is absent. The precursor compound can be selected from the group consisting of sulfur compounds of Formulae (I)-(IV) and selenium compounds of Formulae (V) and (VI).

Formula (I) has the structure:

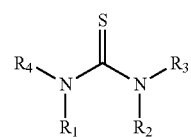

wherein $R_1$, $R_2$, $R_3$, and $R_4$ are independently selected from the group consisting of H, substituted or unsubstituted alkyl, substituted or unsubstituted alkenyl, substituted or unsubstituted cycloalkyl, substituted or unsubstituted cycloalkenyl, and substituted and unsubstituted aryl. Formula (II) has the structure:

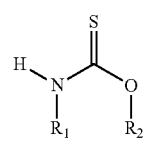

wherein $R_1$ and $R_2$ are independently selected from the group consisting of H, substituted or unsubstituted alkyl, substituted or unsubstituted alkenyl, substituted or unsubstituted cycloalkyl, substituted or unsubstituted cycloalkenyl, and substituted and unsubstituted aryl. Formula (III) has the structure:

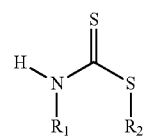

wherein $R_1$ and $R_2$ are independently selected from the group consisting of H, substituted or unsubstituted alkyl, substituted or unsubstituted alkenyl, substituted or unsubstituted cycloalkyl, substituted or unsubstituted cycloalkenyl, and substituted and unsubstituted aryl. Formula (IV) has the structure:

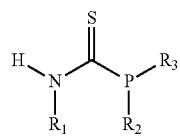

wherein $R_1$, $R_2$, and $R_3$ are independently selected from the group consisting of H, substituted or unsubstituted alkyl, substituted or unsubstituted alkenyl, substituted or unsubstituted cycloalkyl, substituted or unsubstituted cycloalkenyl, and substituted and unsubstituted aryl. Formula (V) has the structure:

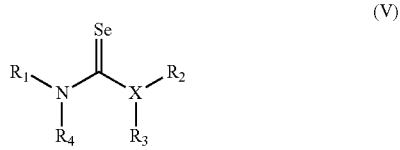

(V)

wherein $R_1$, $R_2$, $R_3$, and $R_4$ are independently selected from the group consisting of H, substituted or unsubstituted alkyl, substituted or unsubstituted alkenyl, substituted or unsubstituted cycloalkyl, substituted or unsubstituted cycloalkenyl, and substituted and unsubstituted aryl; and X is selected from the group consisting of N, O, S, Se, and P; and wherein $R_2$ is absent when X is O, S, or Se. Formula (VI) has the structure:

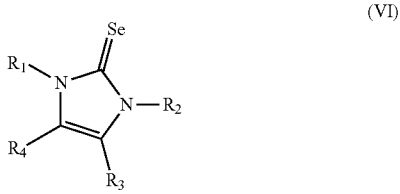

(VI)

wherein $R_1$, $R_2$, $R_3$, and $R_4$ are independently selected from the group consisting of H, substituted or unsubstituted alkyl, substituted or unsubstituted alkenyl, substituted or unsubstituted cycloalkyl, substituted or unsubstituted cycloalkenyl, and substituted and unsubstituted aryl.

In a non-limiting embodiment of the presently disclosed subject matter, a process for preparing a core-shell nanocrystal includes contacting a core nanocrystal with a mixture including a metal salt and a precursor compound selected from the group of sulfur compounds of Formulae (I)-(IV) and selenium compounds of Formulae (V) and (VI), as defined above.

In certain embodiments, the metal salt can be a metal carboxylate, a metal phosphonate, and/or a metal halide. In certain embodiments, the metal salt can be a metal acetylacetonate. In certain embodiments, the metal salt can include a metal oleate. In certain embodiments, the metal can be Pb, Cd, Cu, Zn, In, Ga, Hg, Fe, Mo, and/or Mn. In certain embodiments, the metal can be Cd.

In certain embodiments, the precursor compound can include a sulfur compound of Formula (I), as defined above. In certain embodiments, $R_1$ and $R_2$ of the sulfur compound of Formula (I) can be unsubstituted alkyl, unsubstituted alkenyl, unsubstituted cycloalkyl, and substituted or unsubstituted aryl. The sulfur compound of Formula (I) can be N-phenyl-N'-ortho-tolylthiourea. The sulfur compound of Formula (I) can be N-phenyl-N'-2-ethylhexylthiourea. The sulfur compound of Formula (I) can be N-n-hexyl-N',N'-di-n-butylthiourea. The sulfur compound of Formula (I) can be N-phenyl-N'-n-dodecylthiourea. The sulfur compound of Formula (I) can be N-n-hexyl-N',N'-di-n-octylthiourea. The sulfur compound of Formula (I) can be N,N-diallyl-N-n-butyl-selenourea.

In certain embodiments, the precursor compound can include a selenium compound of Formula (V), as defined above.

In certain embodiments, the nanocrystals can include nanocrystals having a median particle size in a range from about 2 nm to about 8 nm. In certain embodiments, the nanocrystals can include nanocrystals having a narrow particle size distribution such that the standard deviation ($\sigma$) of the particle size distribution is less than or equal to 13% of the median particle size of the nanocrystals.

In a non-limiting embodiment of the presently disclosed subject matter, nanocrystals include at least one semiconductor material selected from the group consisting of metal sulfide and metal selenides. The nanocrystals have a narrow particle size distribution such that the standard deviation ($\sigma$) of the particle size distribution is less than or equal to 13% of the median particle size of the nanocrystals. In certain embodiments, the nanocrystals can include nanocrystals having a narrow particle size distribution such that the standard deviation ($\sigma$) of the particle size distribution is less than or equal to 8% of the median particle size of the nanocrystals. In certain embodiments, the semiconductor material can include lead sulfide (PbS). In certain embodiments, the nanocrystals can include nanocrystals having a median particle size of about 5 nm, and the standard deviation ($\sigma$) of the particle size distribution can be less than or equal to about 0.4 nm. In certain embodiments, the nanocrystals can include nanocrystals having a median particle size of about 7 nm, and the standard deviation ($\sigma$) of the particle size distribution can be less than or equal to about 0.6 nm.

BRIEF DESCRIPTION OF THE DRAWINGS

Further features and various advantages of the disclosed subject matter will be more apparent from the following detailed description of the embodiments and the accompanying drawings in which:

FIG. 9 shows the relationship between reaction rate of a sulfur precursor compound and concentration of nanocrystals formed.

FIG. 19A presents an absorbance spectrum for zinc blende CdSe nanocrystals. FIG. 19B presents an absorbance spectrum for wurtzite CdSe nanocrystals. FIG. 19C presents an absorbance spectrum for ZnSe nanocrystals. FIG. 19D presents an absorbance spectrum for $Cu_{2-x}Se$ nanocrystals.

DETAILED DESCRIPTION

Figure 1:
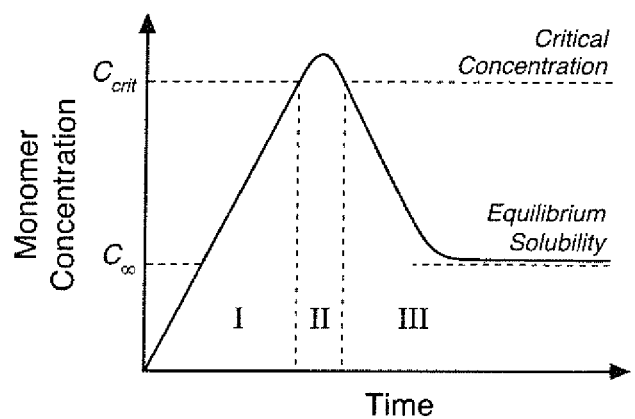
FIG. 1 depicts homogeneous nucleation and growth reactions according to the La Mer model, in which superstation is caused by precursor conversion reaction that supplies monomers to the growth medium.
Figure 2:
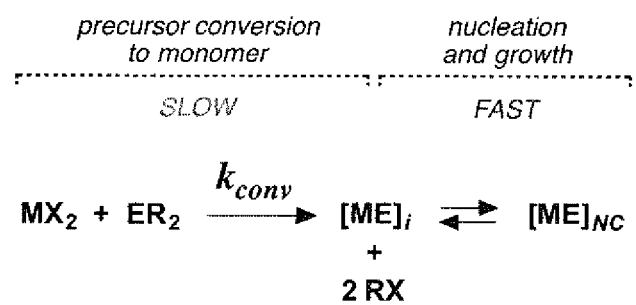
FIG. 2 is a scheme showing a generalized mechanism of precursor-limited homogeneous nucleation and growth of nanocrystals.

The disclosed subject matter relates to metal chalcogenide nanocrystals. The disclosed subject matter relates to quantum dots, i.e., nanocrystals made of semiconducting materials that exhibit quantum mechanical properties. The disclosed subject matter provides sulfur and selenium precursor compounds useful for preparing nanocrystals as well as processes for preparing nanocrystals. The presently disclosed precursor compounds can have well-defined reactivity, which can enable preparation of nanocrystals of predictable, well-defined size. Nanocrystals containing one semiconductor material can be prepared as well as core-shell nanocrystals.

As used herein, the term "alkyl" refers to saturated aliphatic groups. Alkyl groups can be straight chain (e.g., ethyl, n-propyl, n-butyl, n-hexyl, n-octyl, n-decyl, n-dodecyl) or branched chain (e.g., i-propyl, s-butyl).

As used herein, the term "alkenyl" refers to an unsaturated aliphatic group having at least one carbon-carbon double bond (C=C). Alkenyl groups can be straight chain (e.g., allyl, homoallyl) or branched (e.g., prenyl).

As used herein, the term "cycloalkyl" refers to a saturated aliphatic carbon-based cyclic group. Cycloalkyl groups can include one ring or more than one ring. By way of non-limiting example, cycloalkyl groups can include cyclopropyl, cyclobutyl, cyclopentyl, cyclohexyl, cycloheptyl, and cyclooctyl.

As used herein, the term "cycloalkenyl" refers to an unsaturated aliphatic carbon-based cyclic group having at least one carbon-carbon double bond (C=C). Cycloalkenyl groups can include one ring or more than one ring.

As used herein, the term "aryl" refers to an unsaturated, aromatic carbon-based cyclic group. Aryl groups can include one ring or more than one ring. By way of non-limiting example, aryl groups can include phenyl, naphthyl, tolyl, and xylyl groups.

As used herein, the term "carboxylate" refers to a moiety of formula $RCO_2^-$, wherein R is an alkyl, cycloalkyl, aryl, or another carbon-containing group. By way of non-limiting example, carboxylate groups can include oleate, acetate, propionate, butyrate, hexanoate, octanoate, decanoate, dodecanoate, tetradecanoate, hexadecanoate, and octadecanoate.

As used herein, the term "phosphonate" refers to a moiety of formula $RPO_3^{2-}$ and/or $RPO_3H^-$ wherein R is an alkyl, cycloalkyl, aryl, or another carbon-containing group. By way of non-limiting example, phosphonate groups can include $CH_3PO_3^{2-}$, $PhPO_3^{2-}$, $CH_3(CH_2)_{13}PO_3^{2-}$, and $CH_3(CH_2)_{17}PO_3^{2-}$.

As used herein, the term "halide" refers to a moiety of formula $X^-$, wherein X is a halogen, i.e., fluorine, chlorine, bromine, iodine, or astatine.

As used herein, the terms "group" and "moiety" refer to parts of a larger composition, compound, molecule, or structure. The terms "group" and "moiety" can also refer to an anion or cation within an ionic salt or ionic complex.

As used herein, the term "substituted" means that a group can be further substituted by replacement of one or more hydrogen radicals with one or more groups selected from oxygen, nitrogen, sulfur, alkyl, alkenyl, alkynyl, aryl, halo, haloalkyl, haloalkenyl, haloalkynyl, haloaryl, hydroxy, alkoxy, carboxy, haloalkoxy, nitro, nitroalkyl, nitroalkenyl, nitroalkynyl, nitroaryl, nitroheterocyclyl, azido, amino, alkylamino, alkenylamino, alkynylamino, arylamino, benzylamino, acyl, alkenylacyl, alkynylacyl, arylacyl, acylamino, acyloxy, aldehydo, alkylsulfonyl, arylsulfonyl, alkylsulfonylamino, arylsulfonylamino, alkylsulfonyloxy, arylsulfonyloxy, heterocyclyl, heterocycloxy, heterocyclylamino, haloheterocyclyl, alkylsulfenyl, arylsulfenyl, carboalkoxy, carboaryloxy, mercapto, alkylthio, arylthio, acylthio, and the like.

As used herein, the term "surfactant" refers to compounds that can lower the surface tension (interfacial tension) between two liquids or between a liquid and a solid. In certain applications, surfactants can act as ligands for metal salts and/or for nanocrystals. For example, in certain non-limiting embodiments, a carboxylate or phosphonate complex can act as a surfactant.

As used herein, the term "about" or "approximately" means within an acceptable error range for the particular value as determined by one of ordinary skill in the art, which will depend in part on how the value is measured or deteiuiined, i.e., the limitations of the measurement system. For example, "about" can mean a range of up to 20%, up to 10%, up to 5%, and or up to 1% of a given value.

In certain embodiments, the metal salts of the presently disclosed subject matter can include one or more metal carboxylates, metal phosphonates, and metal halides. In certain embodiments, the metal salt can include a metal acetylacetonate. In certain embodiments, the metal can be Pb, Cd, Cu, Zn, In, Ga, Hg, Fe, Mo, and/or Mn. In certain embodiments, the metal can be Pb. In certain embodiments, the metal can be Cd. In certain embodiments, the metal can be Zn.

Precursor compounds of the presently disclosed subject matter can be of the general formula:

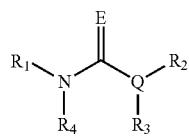

wherein E can be S or Se; Q can be N, O, S, Se, or P; $R_1$, $R_2$, $R_3$, and $R_4$ can be independently selected from the group consisting of H, substituted or unsubstituted alkyl, substituted or unsubstituted alkenyl, substituted or unsubstituted cycloalkyl, substituted or unsubstituted cycloalkenyl, and substituted and unsubstituted aryl, or $R_3$ and $R_4$, taken together, can form a ring, which can be substituted or unsubstituted; with the proviso that when Q is O, S, or Se, $R_2$ is absent.

Precursor compounds of the presently disclosed subject matter can also be thiocarbonate compounds of the general formula:

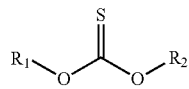

wherein $R_1$ and $R_2$ can be independently selected from the group consisting of H, substituted or unsubstituted alkyl, substituted or unsubstituted alkenyl, substituted or unsubstituted cycloalkyl, substituted or unsubstituted cycloalkenyl, and substituted and unsubstituted aryl, or $R_1$ and $R_2$, taken together, can form a ring, which can be substituted or unsubstituted. Thiocarbonates can be prepared on multigram scale, as shown in Scheme 1 below, by mixing thiophosgene or an alkoxythiocarbonyl chloride with one or more alcohols in the presence of a base.

Scheme 1. Exemplary Syntheses of Thiocarbonates

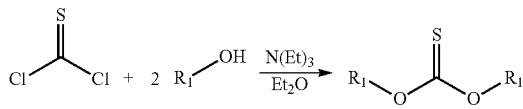

-continued

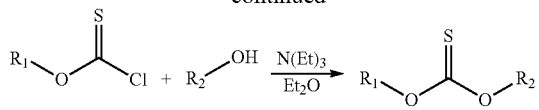

In the compounds of Scheme 1, $R_1$ and $R_2$ can independently be substituted or unsubstituted alkyl, substituted or unsubstituted alkenyl, substituted or unsubstituted cycloalkyl, substituted or unsubstituted cycloalkenyl, and substituted and unsubstituted aryl. While $N(Et)_3$ (triethylamine) and $Et_2O$ (diethyl ether) are shown as exemplary base and solvent, respectively, it should be understood that other bases and solvents can be used to prepare thiocarbonates according to the general procedure of Scheme 1.

Substituted thioureas are another useful class of sulfur precursors because of their stability in air, low toxicity, and the ease of modifying their organic substituents to tune their reactivity. A large library of these compounds can be prepared from inexpensive, commercially-available substituted isothiocyanates and primary or secondary amines. The thioureas are readily prepared on multigram scale, as shown in Scheme 2 below, by mixing equimolar amounts of electrophilic substituted isothiocyanates and primary or secondary amines at room temperature:

Scheme 2. Synthesis of Substituted Thioureas

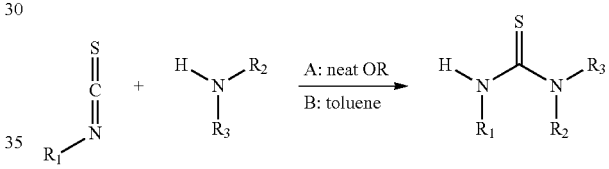

By way of non-limiting example, in the compounds of Scheme 2, $R_1$ can, in certain embodiments, be substituted or unsubstituted alkyl (e.g., t-butyl, isopropyl, n-hexyl), substituted or unsubstituted cycloalkyl (e.g., cyclohexyl), or substituted or unsubstituted aryl (e.g., p-X-Ph, where X is OMe, Me, H, Cl, $CF_3$, CN, $NO_2$). $R_2$ and $R_3$ can be H, substituted or unsubstituted alkyl (e.g., n-hexyl, n-octyl, n-dodecyl), or substituted or unsubstituted aryl (e.g., Ph). Further embodiments of the processes and compounds presented in Scheme 2 are included in the Examples.

Sulfur precursors, including thioureas, thiocarbamates, and other sulfur-containing precursor compounds described herein, can also be prepared via numerous other routes known in the art. For example, thioureas can be prepared from carbon disulfide, from thiophosgene, and/or from derivatives of thiophosgene.

Certain thioureas that can be made using this technique (Scheme 2) have been synthesized and their structures verified using $^1H$ and $^{13}C$ NMR, mass spectrometry, and elemental analysis. Further details are provided in the Examples. The selection of isothiocyanate and amine can be important, however, because amines such as anilines are not always sufficiently nucleophilic to react with the more electron rich alkyl-substituted isothiocyanates at room temperature. However, a wide variety of N,N'-alkylarylthioureas (see 2a-2f in FIG. 3) can be easily obtained. A variety of aryl-substituted isothiocyanates are commercially available.

Figure 4:
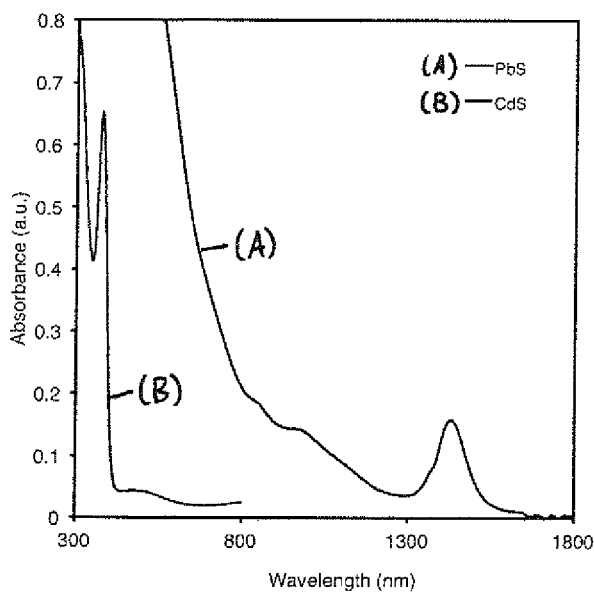
FIG. 4 is a representative absorbance spectra of cadmium sulfide (red) and lead sulfide (blue) nanocrystals synthesized using N-phenyl-N'-dodecyl-thiourea.
Figure 5:
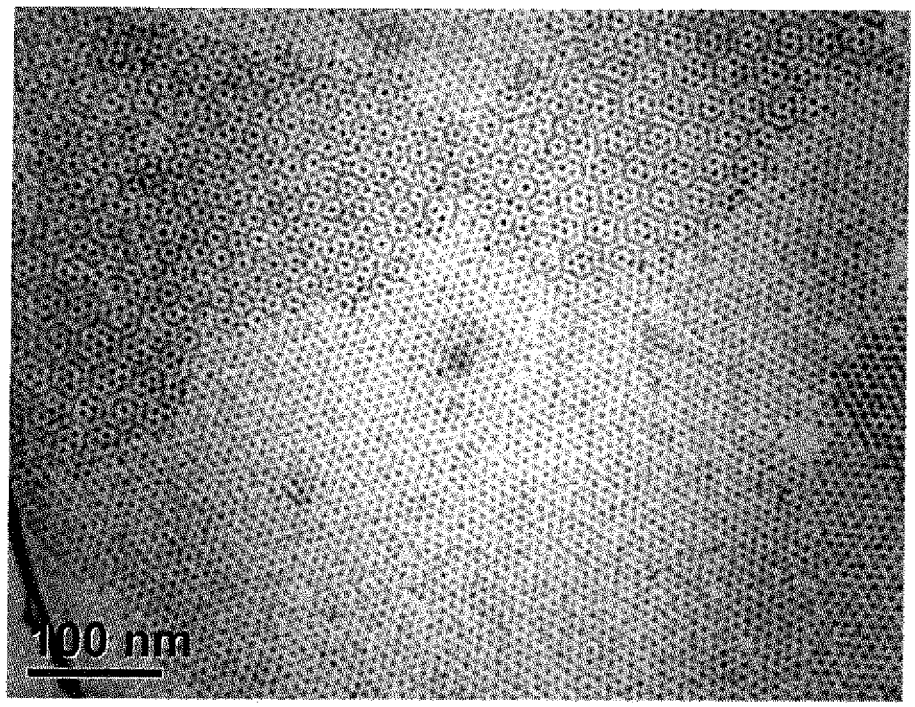
FIG. 5 is a transmission electron micrograph showing highly monodisperse PbS synthesized during a kinetics trial using N-phenyl-N'-n-dodecyl-thiourea.

Preparation of several metal sulfide colloidal nanocrystals has proven possible using the combination of thiourea and metal carboxylate, phosphonate, and/or halide precursors, including PbS, CdS, and CuS. An even wider variety of metal sulfide materials are accessible using this approach. Metal sulfide nanocrystals can be prepared by injecting a solution of thiourea in a solvent (e.g., an alkane, alkene, amine, phosphine, ether (e.g., dialkyl ether, diaryl ether, aryl alkyl ether), ester, nitriles, arene, alcohol, acid, or combination thereof) into a solution of the corresponding metal salt (e.g., a metal carboxylate, phosphonate, halide, or combination thereof) in a solvent (e.g., an alkane, alkene, amine, phosphine, ether (e.g., dialkyl ether, diaryl ether, aryl alkyl ether), ester, nitriles, arene, alcohol, acid, or combination thereof) at an appropriate temperature. In certain embodiments, PbS nanocrystals can be prepared at temperatures between about 90° C. and about 240° C. CdS nanocrystals can be prepared at temperatures between about 180° C. and about 240° C. For example, both PbS and CdS nanocrystals can be synthesized by injecting a solution of the desired thiourea dissolved in diphenyl ether ($Ph_2O$) into a solution of the corresponding metal carboxylate (either $Pb(oleate)_2$ or $Cd(tetradecanoate)_2$) in hexadecane or 1-octadecene at 120° C. for PbS or via heating from room temperature to 240° C. for CdS. Absorbance spectra of representative reactions are shown in FIG. 4 and a transmission electron micrograph of PbS nanocrystals is shown in FIG. 5 demonstrating that nanometer scale crystals with narrow size distributions ($\sigma \leq 0.2$ nm) are readily accessible.

Figure 6:
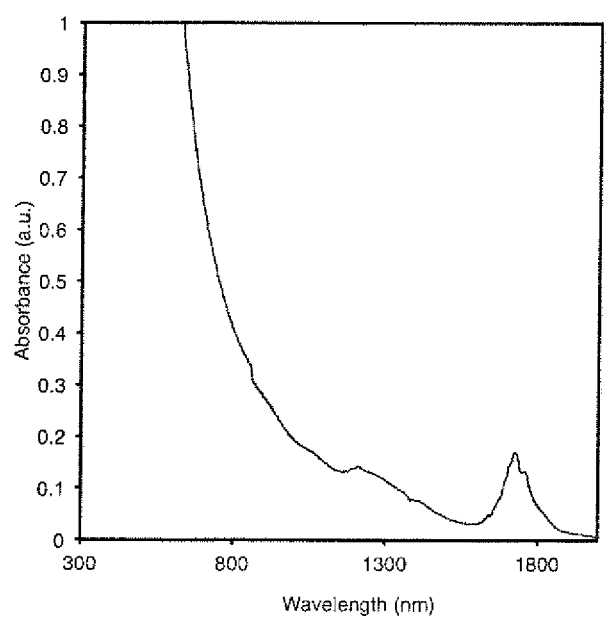
FIG. 6 is a representative absorbance spectrum of lead sulfide synthesized on >5 g scale.

The synthetic ease allows a diverse family of thioureas with different substitution to be accessed by mixing the two components. By adjusting the number and type of substituents, the conversion reactivity can in principle be readily tuned over a wide range. The tunable reactivity of the precursor enables identification of precursors that are conveniently utilized on large scales. By way of non-limiting example, by using N-n-hexyl-N',N'-di-n-butylthiourea as the precursor, lead sulfide nanocrystals could be synthesized on a greater than 5 g scale (e.g., up to 10 g or more). By using lead oleate as the precursor, less than 125 mL of reaction solvent were required, while maintaining narrow size distribution (FIG. 6).

Figure 3:
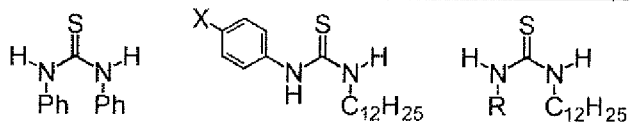
FIG. 3 is a scheme and table showing the effect of structural changes of thiourea precursor compounds on reaction rate.
Figure 7:
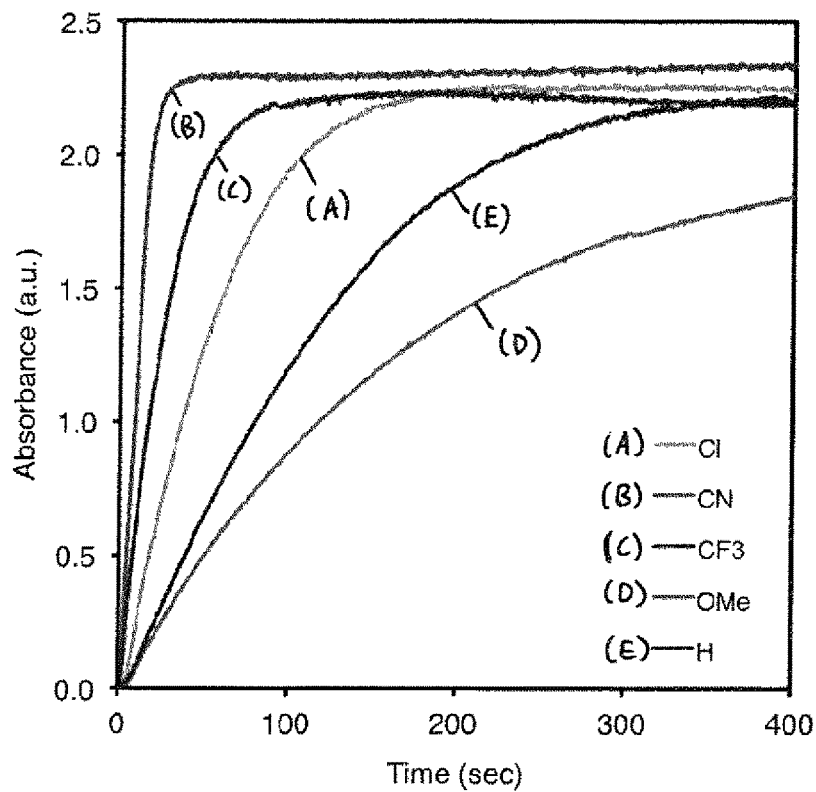
FIG. 7 depicts kinetics traces showing the appearance of absorbance at 400 nm due to the formation of PbS from various N-(para-substituted-phenyl)-N'-n-dodecyl-thioureas.

In order to determine how structural changes to the thiourea affect the precursor conversion rate, we monitored the rate of PbS formation in-situ across a variety of thiourea precursors and temperatures. This was accomplished by monitoring the absorbance at $\lambda=400$ nm, where the size-independent PbS absorbance is proportional to the concentration of PbS. This analysis shows that quantitative conversion of the thiourea can be achieved at this low temperature (>95% yield). Example kinetics traces are shown in FIG. 7, where the formation of PbS appears first order. The precursors of FIG. 7 are the para-substituted N,N'-alkylarylthioureas of FIG. 3. Pseudo first order rate constants extracted from the kinetics traces are shown in FIG. 3, across a range of temperature from 120-150° C. Relative pseudo first order rate constants were extracted, in some cases at more than one temperature for the same thiourea. Procedures for the kinetics experiments are provided in the Examples. As shown in FIG. 3, adjusting substitution of the sulfur precursor compound can tune the rate of PbS nanoparticle formation over more than four orders of magnitude. In FIG. 3, the precursor thiourea compounds tested were of the general formula:

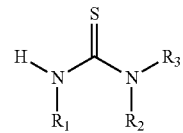

wherein $R_3$ is H and $R_1$ and $R_2$ are as defined in FIG. 3.

Figure 8:
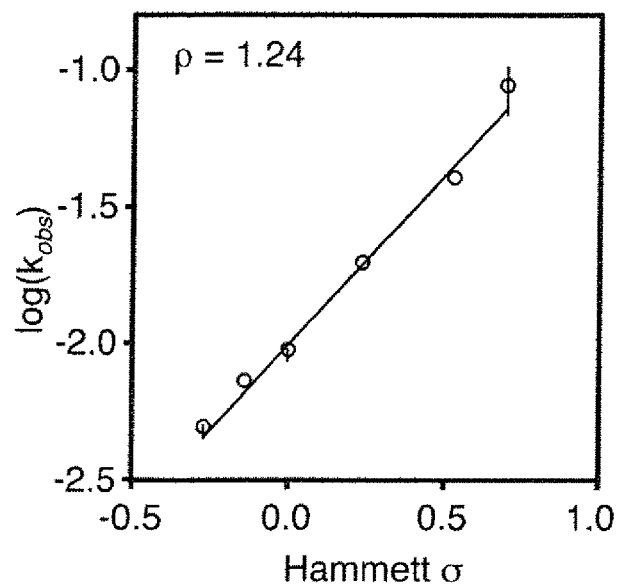
FIG. 8 is a Hammett plot showing PbS formation rate vs. Hammett $\sigma$, as obtained from kinetics experiments.

In certain non-limiting embodiments involving reactions of thioureas and Pb salts, the rate of conversion can increase when more electron poor thioureas are used; as shown in FIG. 3, N,N'-diphenylthiourea (1) converted most rapidly while N-n-hexyl-N'-n-dodecylthiourea (6) reacted least rapidly. To eliminate the influence of steric differences on the rate, a series of para-substituted N-phenyl-N'-n-dodecyl thioureas (2a-2f) were analyzed. The log of the pseudo-first order rate constants ($\log(k_{obs})$) are plotted versus the Hammett sigma parameter in FIG. 8 where a linear relationship with a positive slope ($\sigma=1.24$) is observed. This trend indicates that a buildup of negative charge in the transition state is stabilized by electron withdrawing substituents. The conversion of thiourea in aqueous solution can be accelerated under basic conditions, and deprotonation of the thiourea can be used as a pre-equilibrium procedure to sulfide elimination. Conversion is accelerated in the presence of aliphatic amines and appears to be retarded in the presence of added carboxylic acids. N,N,N'-trisubstituted thioureas can be relatively less reactive, can require reaction temperatures of 150° C. or above, and can produce large aggregated lead sulfide nanocrystals.

The rate of solute supply during nucleation is known to influence the number of nanocrystals. As a consequence, control over conversion kinetics allows one to tune nanocrystal size, shape, and composition. Previous experimental and theoretical work has shown that the final number of nanocrystals is correlated with the initial rate of precursor conversion, where faster rates produce greater numbers of nanocrystals. Thus, in reactions where the precursor conversion is quantitative, and when Ostwald ripening does not significantly change the number of nanocrystals, a desired size can in principle be obtained by tuning the conversion rate.

Figure 9A:
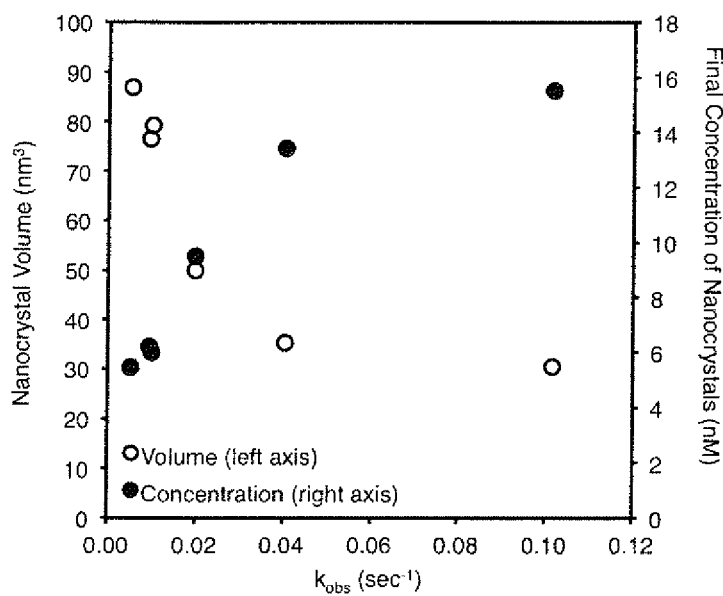
FIG. 9A is a plot showing the relationship between PbS formation rate and final nanocrystal volume and concentration.
Figure 9B:
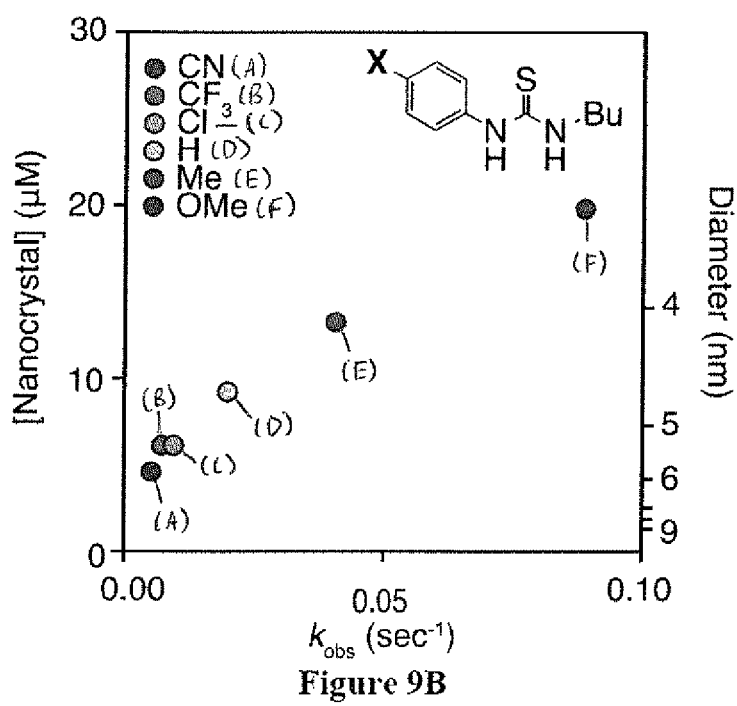
FIG. 9B is s plot showing the relationship between PbS formation rate and final nanocrystal size (diameter) and concentration.

To determine whether this principle applies in the present syntheses, final nanocrystal volumes were measured from the wavelength of the lowest energy absorption, by assuming a spherical shape and the molar volume of bulk PbS, and used to compute the number of nanocrystals. The final nanocrystal concentration from precursors 2a-2f (as defined in FIG. 3) is plotted versus the respective $k_{obs}$ in FIG. 9. FIG. 9 shows the relationship between reaction rate of a sulfur precursor compound and concentration of nanocrystals formed. FIG. 9A is a plot showing the relationship between PbS formation rate and final nanocrystal volume and concentration. FIG. 9B is s plot showing the relationship between PbS formation rate and final nanocrystal size (diameter) and concentration. Both FIG. 9A and FIG. 9B indicate that an increase in reaction rate leads to greater numbers of nanocrystals. Because these reactions achieve complete conversion of the precursor and Ostwald ripening is slow, the final volume of the nanocrystals correspondingly changes with rate, with the fastest reactions resulting in the smallest nanocrystals. Furthermore, these results demonstrate that thioureas can be used to obtain a desired nanocrystal size in quantitative yield via selection of the appropriate precursor. FIG. 9B establishes that smaller nanocrystals can be obtained from faster-reacting precursors.

Gaining control over size by adjusting the precursor structure can produce an advantage over certain methods to synthesize nanocrystals that control size by limiting the extent of conversion or by adjusting the concentrations of surfactants. This approach can also alter the composition of the final reaction medium and can influence the nanocrystal composition; particularly by changing the composition of surfactants, and the concentration of remaining metal surfactant complexes. Work on CdSe, CdS, PbS, and PbSe nanocrystals has shown that nanocrystal stoichiometry is in equilibrium with the reaction medium, making it sensitive to the concentration of remaining metal carboxylate precursor.

Controlling nanocrystal size by controlling precursor reaction rate rather than modifying crystallization medium (e.g., reaction temperature, solvent, surfactant concentration) or limiting conversion can greatly simplify nanocrystal synthesis and isolation. For example, changes in the surfactant composition also the nanocrystals surface chemistry and resultant properties. Similarly, partial precursor conversion requires these starting materials be separated from the reaction mixture, a process that is complicated by the polymeric structure and low solubility of zinc, cadmium, and lead carboxylates, phosphonates, and halides. This issue can be important given that metal surfactant complexes reversibly bind nanocrystal surfaces and dramatically impact the photoluminescence quantum yield. By contrast, in the case of PbS nanocrystals presented above, the quantitative conversion allows the final ratio of excess lead and lead sulfide to be precisely controlled. Gaining control over this ratio is not only important to the nanocrystal stoichiometry, but also to the isolation procedures, where the remaining lead oleate is removed. Thus, gaining control over the final size by adjusting the precursor structure can allow one to also control the final composition of the reaction mixture and subsequent isolation process. Inconsistencies in nanocrystal isolation can thus begin mitigated, because the composition of the crude reaction mixture is set by the starting composition, rather than a consequence of the extent of conversion.

The present disclosure provides processes for preparing nanocrystals on large scale. For example, in certain embodiments, lead sulfide nanocrystals can be prepared on large scale from lead oleate. Lead oleate can be prepared by dissolving lead oxide in aqueous hydrofluoroboric acid, followed by neutralization in the presence of oleic acid. In this manner, hydroxide-free lead oleate can be synthesized, purified, and dried in 100 gram batches. Lead oleate can also be prepared on large scale via lead trifluoroacetate. Reaction of lead(II) oxide with trifluoroacetic acid and trifluoroacetic anhydride can provide lead trifluoroacetate, which can then react with oleic acid and a base to provide lead oleate. Further details of the synthesis of lead oleate are provided in the Examples.

Preformed lead oleate allows the synthesis of lead chalcogenide nanocrystals to be conducted in low boiling solvents like 1-octene (b.p. 122-123° C.), which can be conveniently distilled from the crude reaction mixture under vacuum. This technique can substantially reduce solvent waste and cost and can allows a standard purification procedure to be optimized at high concentration, providing reproducible control over the final nanocrystal composition. The processes can be performed with high reaction concentrations, for example allowing more than 1 gram of nanocrystals to be prepared in 20 mL of reaction mixture at scales as large as 250 mL. By way of non-limiting example, three batches of nanocrystals with λ=950 nm were prepared on greater than 10 gram scale of purified nanocrystals, providing nanocrystals isolated with 2 oleate ligands per $nm^2$ of surface area. Further details of large scale preparation of lead sulfide nanocrystals are provided in the Examples.

In certain non-limiting embodiments involving reactions of thioureas and Cd salts, the rate of conversion can decrease when more electron poor thioureas are used. That is, the rate of conversion can increase when more electron rich thioureas are used. The flexible reactivity of precursor compounds allows a precursor to be selected to match the required reaction temperature or metal salt. By way of non-limiting example, CdS nanocrystals could be synthesized from cadmium carboxylate using N,N,N'-trialkyl-substituted thioureas, which convert at the temperature range required for crystallization (160-200° C.). Similarly, CuS nanocrystals could be synthesized from copper (II) acetylacetonate, N-phenyl-N'-hexyl-thiourea, oleic acid, and oleylamine.

The tunability of the precursor conversion kinetics allows a desired conversion rate to be selected for a particular reaction temperature, or a particular set of reaction conditions. This tunability can in principle make substituted thioureas broadly useful, for the synthesis of a variety of metal sulfides and nanocrystal heterostructures, such as core-shell, dot-in-rod, or alloyed nanocrystals. Controllable supersaturation can help to suppress homogeneous nucleation during shell growth that occurs with uncontrolled reactivity of existing sulfur precursors used in core-shell QD synthesis. Similarly, tunable kinetics can allow core-shell interfaces to be graded by intermixing the chalcogens—an important aspect of their structure, having consequences for the photoluminescence quantum yield. Tunability of the reaction rate can be of utility in the synthesis of nanocrystal heterostructures, where methods should precisely control the steady state supersaturation to prevent homogeneous nucleation and to grade the composition of interfaces.

In certain embodiments, selenium and sulfur precursors with similar conversion kinetics can be identified, along with temperatures useful in the synthesis of different forms of cadmium selenide (CdSe), e.g., wurtzite and zinc blende. Changing the temperature of reaction can affect the crystal phase of nanocrystal products. By way of non-limiting example, and as described in the Examples, wurtzite CdSe can be prepared at about 370° C. when an appropriate selenium precursor is used. By way of non-limiting example, and as described in the Examples, zinc blende CdSe can be prepared at about 240° C. when an appropriate selenium precursor is used. For example, N,N'-disubstituted 2-selenoimidazolines can allow quantitative formation of wurtzite QDs with the dimensions needed to prepare red emitting, green emitting, and other wavelength phosphors. See FIG. 19. Certain less reactive sulfur precursor compounds can react at a rate that is on the order of the cyclic selenoureas.

Figure 10:
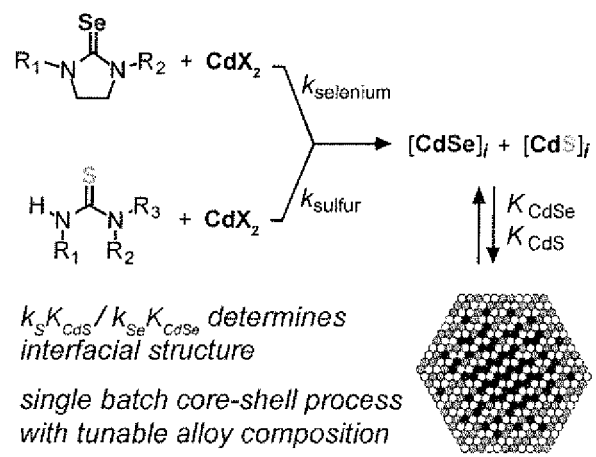
FIG. 10 is a simplified scheme presenting preparation of graded CdSe/CdS nanocrystals in accordance with one embodiment of the present disclosure.

Once suitable sulfur and selenium precursors are identified, one pot syntheses of alloy and core-shell structures can be developed, as shown in FIG. 10. Homogeneous alloyed nanocrystalline quantum dots can also be of interest because the band gap and luminescence wavelength can be tuned by the composition of homogeneous alloys.

Figure 11:
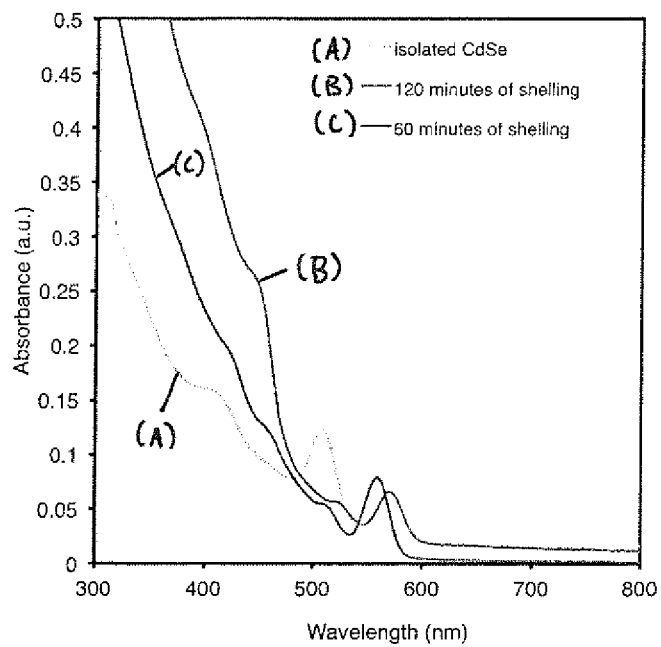
FIG. 11 is an absorbance spectra of isolated nanocrystals prior to shelling, and aliquots removed 60 and 120 minutes through the shelling procedure.

To demonstrate the broad utility of these precursors for preparation of core-shell nanocrystals, a procedure was established for using substituted thioureas for shelling CdSe nanocrystals. Using insight obtained from previous shelling efforts, one of the less reactive members of the precursor library, N-n-hexyl-N'-n-dodecylthiourea was used as the sulfur source. The reaction temperature (of 210° C.) coupled with the slow addition of precursors resulted in the growth of high-quality shells that increase the photoluminescence of the nanocrystals. FIG. 11 shows the progression of the absorbance of the nanocrystals over the course of the shelling process. The increase in high-energy absorbance and small red-shift of the lowest energy electronic transition are indicative of shelling. In certain non-limiting embodiments using this exemplary method, the quantum yield of CdSe nanocrystals can increase from 7% to about 25%.

Figure 12:
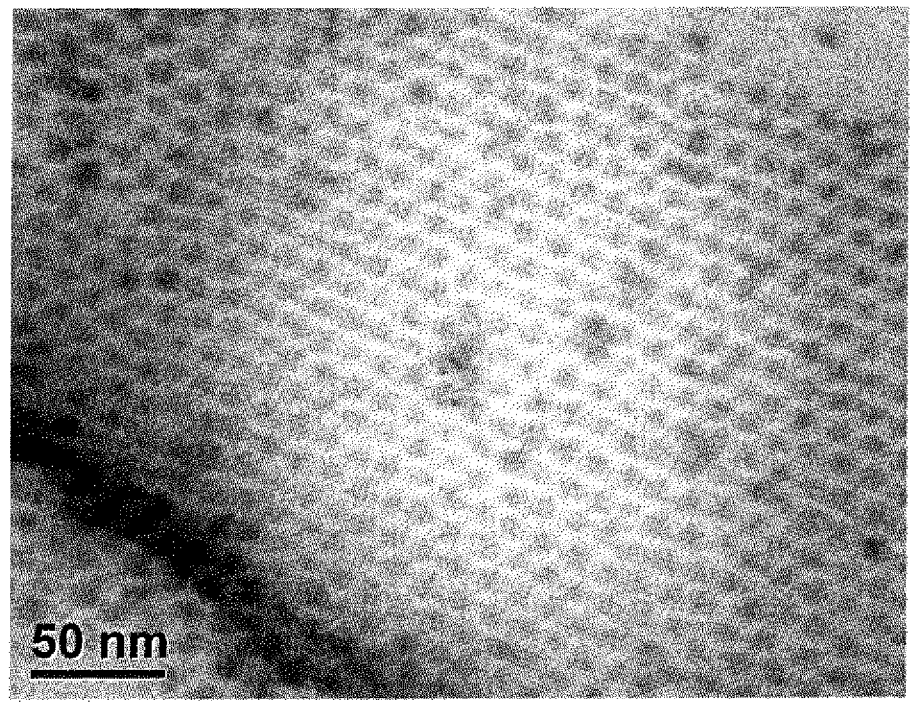
FIG. 12 is a transmission electron micrograph showing highly monodisperse CuS synthesized in accord with the disclosed subject matter.

In another embodiment, CuS nanocrystals are synthesized. CuS is an interesting metal sulfide system, especially in light of the potential solar applications of related CZTS and CIGS materials. CuS nanocrystals were synthesized by combining copper(II) acetylacetonate, oleic acid, and oleylamine in 1-octadecene, heating to 160° C., and then injecting a thiourea dissolved in diphenyl ether. FIG. 12 is a TEM micrograph showing the resulting CuS. Similar to other sulfur precursors, because substituted thioureas can be used to make CdS, PbS, and CuS, they can be widely applicable to make other sulfur-containing nanocrystalline materials.

Figure 13:
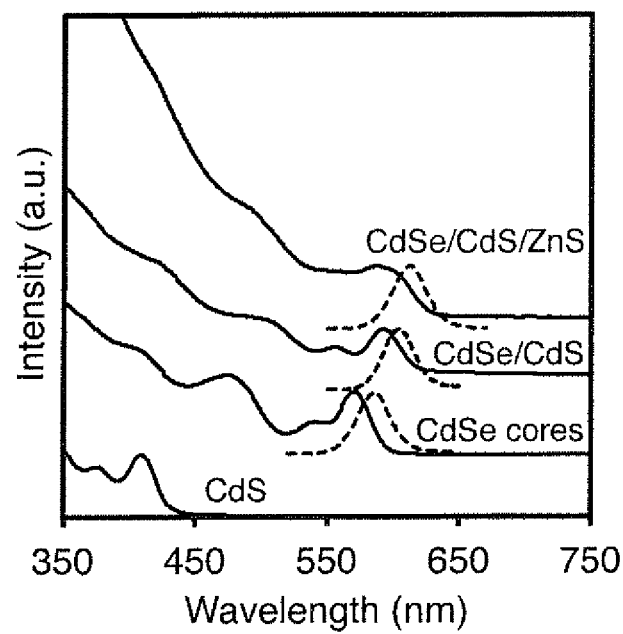
FIG. 13 presents absorbance and fluorescence spectra of CdS nanocrystals and CdSe/CdS/ZnS core/shell/shell heterostructures produced from precursor thioureas, according to one embodiment of the present disclosure.

In certain embodiments, core/shell/shell nanocrystals can be prepared. For example, CdSe/CdS/ZnS core/shell/shell heterostructures were obtained by substituting a relatively unreactive thiourea (N-n-hexyl-N'-di-n-octyl-thiourea) as the sulfur precursor in an existing successive ionic layer adsorption and reaction synthesis (see Examples for details). Exemplary absorbance and fluorescence spectra are presented in FIG. 13. This allowed preparation of samples with similar photoluminescence quantum yields (60+/−5%). However, quantitative conversion of the thiourea allowed sulfur addition to be more precisely controlled. A reduced quantity of precursor could be used, as compared to the sulfur and oleylamine solutions, which only partially convert to the metal sulfide, which can improve overall economy and efficiency.

According to another aspect, the techniques of the disclosed subject matter can be used to prepare di-, tri-, and tetrasubstituted selenourea compounds. In exemplary embodiments, selenourea compounds in the presence of metal salts can be utilized to synthesize high-quality metal selenide nanocrystals with narrow size distributions (e.g., σ=5-11% or 5-13% of median particle size). Selenourea compounds can be utilized as precursors for metal selenide shells on pre-existing nanocrystals. Other selenium-containing precursor compounds related to selenoureas can also be utilized as metal selenide precursors.

For example, and as embodied herein, an exemplary technique for synthesizing di- and trisubstituted selenoureas and related compounds from isocyanides, selenium, and amines, alcohols, thiols, selenols, or phosphines can be conducted as in Scheme 3:

Scheme 3. Preparation of selenium precursor compounds.

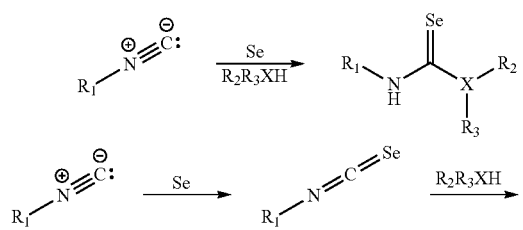

-continued

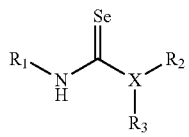

By way of non-limiting example, in the compounds of Scheme 3, $R_1$ can be substituted or unsubstituted alkyl, substituted or unsubstituted cycloalkyl, substituted or unsubstituted alkenyl, substituted or unsubstituted cycloalkenyl, or substituted or unsubstituted aryl; $R_2$ and $R_3$ can independently be H, substituted or unsubstituted alkyl, substituted or unsubstituted cycloalkyl, substituted or unsubstituted alkenyl, substituted or unsubstituted cycloalkenyl, or substituted or unsubstituted aryl; and X can be N, O, S, Se, or P, with the proviso that $R_2$ is absent when X is O, S, or Se. In certain embodiments, X can be N, and selenoureas can be prepared. In certain embodiments, $R_1$ can be an unsubstituted alkyl or unsubstituted cycloalkyl group, e.g., n-butyl, isopropyl, cyclohexyl, or t-butyl. In certain embodiments, $R_2$ and $R_3$ can independently be H, unsubstituted alkyl, or unsubstituted alkenyl (e.g., allyl). In certain embodiments, preparations conducted according to Scheme 3 can be carried out in an ether solvent (e.g., tetrahydrofuran).

Additionally, and as embodied herein, an exemplary technique for synthesizing tetrasubstituted selenourea compounds from imidazolium salts, bases, and selenium can be conducted as in Scheme 4:

Scheme 4. Preparation of selenium precursor compounds.

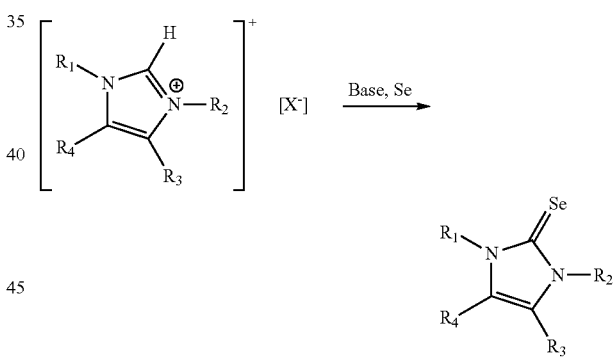

By way of non-limiting example, in the compounds of Scheme 4, $R_1$ can be substituted or unsubstituted alkyl, substituted or unsubstituted cycloalkyl, substituted or unsubstituted alkenyl, substituted or unsubstituted cycloalkenyl, or substituted or unsubstituted aryl; $R_2$ can be H, substituted or unsubstituted alkyl, substituted or unsubstituted cycloalkyl, substituted or unsubstituted alkenyl, substituted or unsubstituted cycloalkenyl, or substituted or unsubstituted aryl; and $R_3$ and $R_4$ can independently be H, substituted or unsubstituted alkyl (e.g., benzyl), substituted or unsubstituted cycloalkyl, substituted or unsubstituted alkenyl, substituted or unsubstituted cycloalkenyl, or substituted or unsubstituted aryl. The base can be various inorganic or organic bases known in the art, e.g., potassium t-butoxide, butyllithium, or sodium hydroxide. By way of non-limiting example, $X^-$ can be $Cl^-$, $Br^-$, $I^-$, $BF_4^-$, or $PF_6^-$.

In addition, and as embodied herein, an exemplary technique for synthesizing symmetric tetrasubstituted selenourea compounds from secondary amines, triethyl orthoformate, and selenium can be conducted as in Scheme 5:

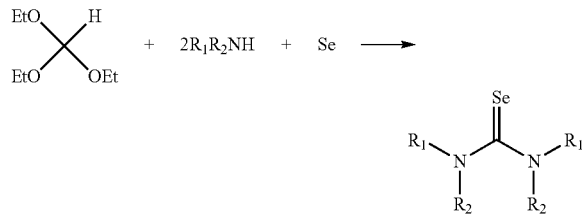

Scheme 5. Preparation of selenium precursor compounds.

By way of non-limiting example, in the compounds of Scheme 5, $R_1$ and $R_2$ can independently be H, substituted or unsubstituted alkyl, substituted or unsubstituted cycloalkyl, substituted or unsubstituted alkenyl, substituted or unsubstituted cycloalkenyl, or substituted or unsubstituted aryl.

Furthermore, and as embodied herein, an exemplary reaction between substituted selenoureas (and related compounds) and metal salts can be conducted as in Scheme 6:

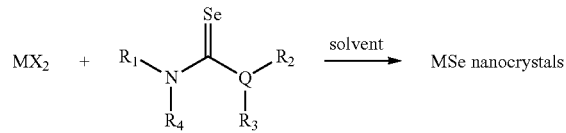

Scheme 6. Preparation of MSe nanocrystals.

The selenourea compounds of Scheme 5 can be prepared according to the various methods for preparation of di-, tri-, and tetrasubstituted selenourea compounds noted above (e.g., in Schemes 3, 4, and 5). By way of non-limiting example, in the metal salts of Scheme 6, X can be a carboxylate, phosphonate, or halide. Suitable solvents for metal selenide preparation can include alkanes, alkenes, amines, phosphines, ethers (including dialkyl ethers (e.g., dibutyl ether), diaryl ethers (e.g., diphenyl ether), aryl alkyl ethers (e.g., anisole), polyethers (e.g., diglyme)), esters, lactones (e.g., gamma-butyrolactone), nitriles (e.g., benzonitrile), arenes, alcohols, and acids. By way of non-limiting example, in certain embodiments preparation of MSe nanocrystals from a metal salt and a selenium-containing precursor compound can be conducted at a temperature in a range from about 80° C. to about 150° C.

Figure 14:
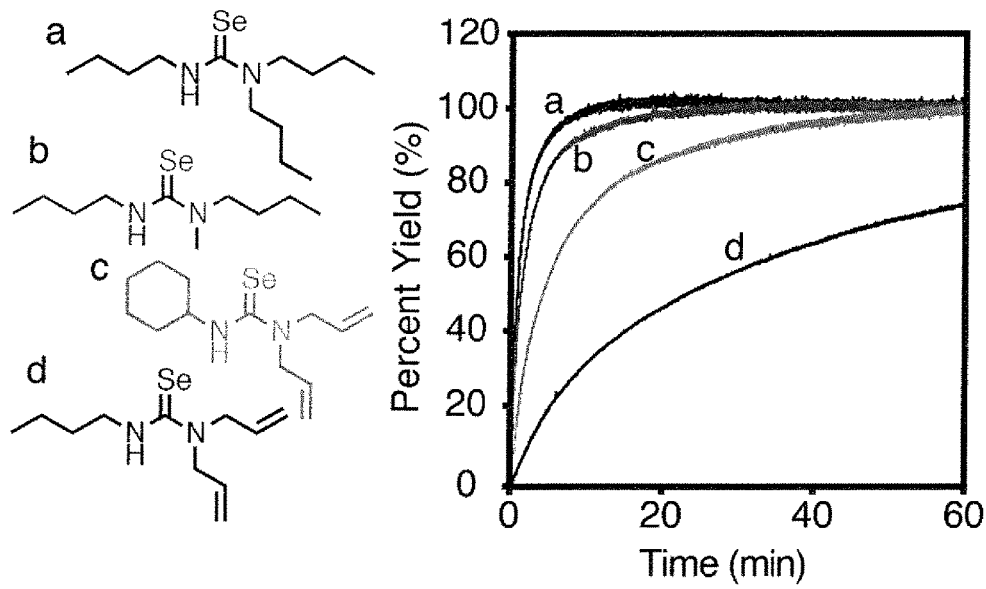
FIG. 14 presents a plot of concentration of PbSe vs. time as measured during preparation of PbSe nanocrystals from certain selenium-containing precursor compounds according to one embodiment of the present disclosure.

Additionally, and as embodied herein, reactions between selenoureas and metal complexes can provide quantitative yields of MSe nanocrystals, within measurement error. Furthermore, the appearance of MSe can be monitored using a dip probe to measure absorbance in situ and established conversions to concentration. FIG. 14 presents a plot of concentration of PbSe vs. time as measured during preparation of PbSe nanocrystals from certain selenium-containing precursor compounds according to one embodiment of the present disclosure. As depicted in FIG. 14, MSe formation can follow a first-order rate dependence. As described in the Examples, kinetics data was collected by monitoring absorbance at 400 nm, where absorbance is size-independent and proportion to concentration of lead selenide formula units.

Figure 15:
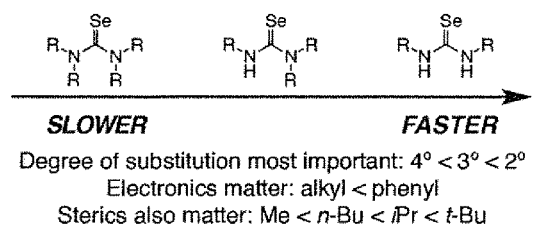
FIG. 15 is a simplified scheme presenting trends in the rate of metal selenide nanocrystal formation with changes in selenium precursor compound structure.

In certain embodiments, the substituents on the selenourea can be varied, and the reaction rate and resultant nanocrystal size can be tuned. Greater degrees of substitution can provide slower rates (disubstituted>trisubstituted>tetrasubstituted). Furthermore, more sterically encumbered selenoureas can react faster than less sterically encumbered selenoureas. More electron deficient selenoureas can react faster than relatively electron right selenoureas. These trends are summarized in FIG. 15. In this manner, faster selenourea conversion can provide a greater number of nanocrystals, at least in part because yield can be considered constant and quantitative, and with the greater number of nanocrystals produced, each nanocrystal can have a smaller size.

Figure 16:
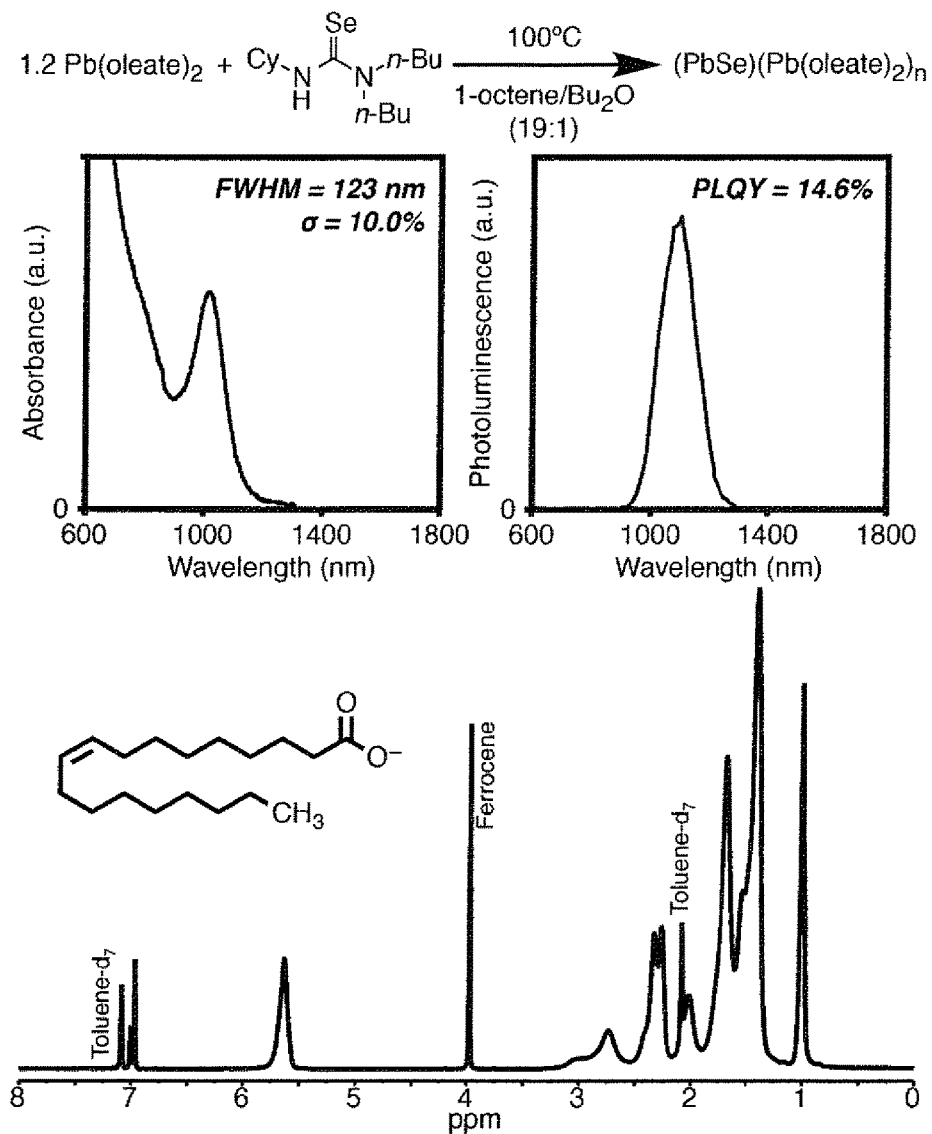
FIG. 16 presents an exemplary metal selenide nanocrystal preparation. A scheme summarizing synthesis of 2.5 nm PbSe nanocrystals is shown at top, with corresponding absorption and photoluminescence spectra below.

An exemplary metal selenide nanocrystal preparation is shown in FIG. 16. A scheme summarizing synthesis of 2.5 nm PbSe nanocrystals is shown at top, with corresponding absorption and photoluminescence spectra below. The size distribution was narrow ($\sigma$=10.0%). The 1H NMR spectrum of the 2.5 nm PbSe nanocrystals is presented at bottom. In this example, the PbSe nanocrystals were found to have a ligand coverage of 3.4±0.3 oleates/nm$^2$, corresponding to a Pb:Se ratio of 1.24±0.1.

Figure 17:
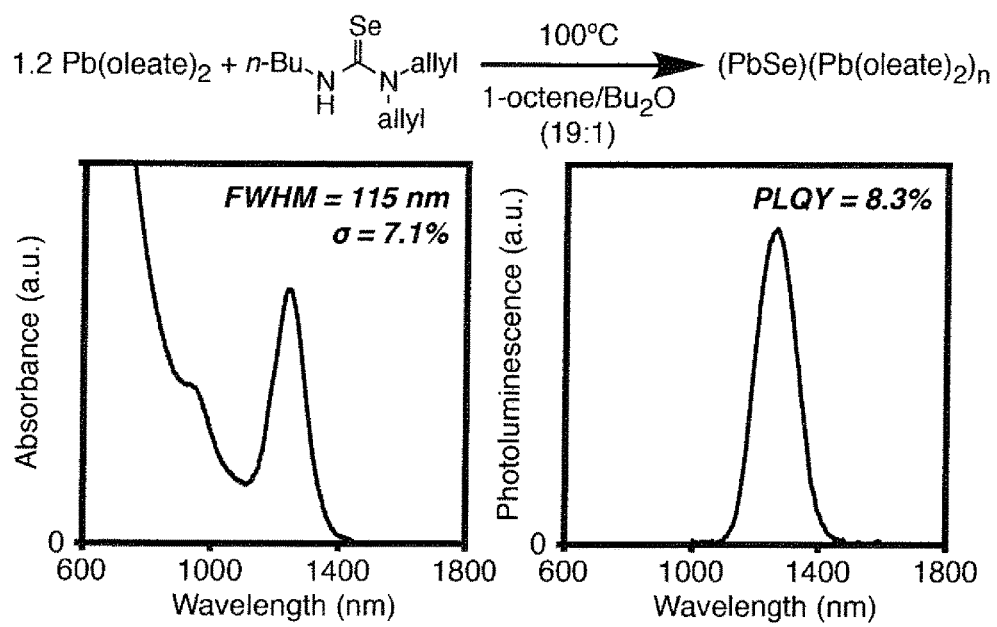
FIG. 17 presents an exemplary metal selenide nanocrystal preparation. A scheme summarizing synthesis of PbSe nanocrystals is shown at top, with corresponding absorption and photoluminescence spectra below.

An additional exemplary metal selenide nanocrystal preparation is shown in FIG. 17. A scheme summarizing synthesis of PbSe nanocrystals is shown at top, with corresponding absorption and photoluminescence spectra below. The size distribution was narrow ($\sigma$=7.1%).

Figure 18:
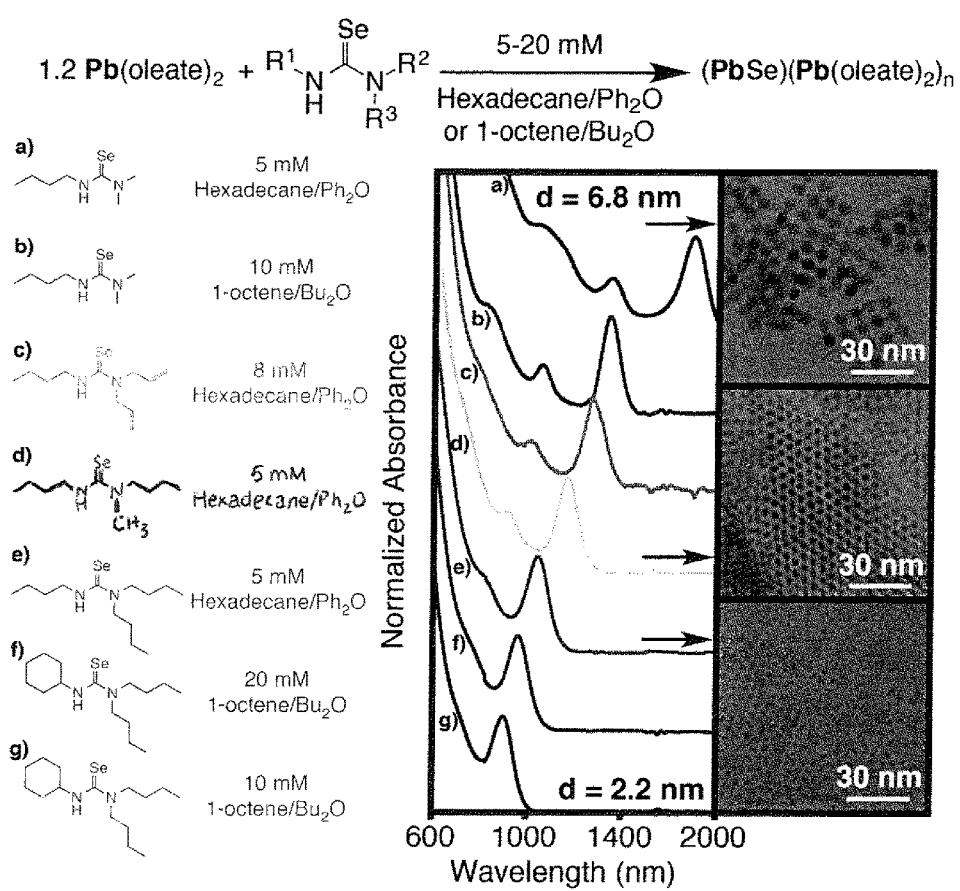
FIG. 18 presents absorbance spectroscopy data and TEM data for PbSe nanocrystals prepared from selenourea precursors in accordance with one embodiment of the present disclosure. The Figure is annotated with the selenourea precursors and solvents used to prepare different PbSe nanocrystals. PbSe nanocrystals are synthesized by the route summarized at the top of the Figure, producing nanocrystals that are characterized by absorbance spectroscopy (left) and TEM of selected samples (right). Conditions used to prepare each sample are provided.

FIG. 18 presents additional absorbance spectroscopy data and TEM data for PbSe nanocrystals prepared from selenourea precursors in accordance with certain embodiments of the present disclosure. The Figure is annotated with the selenourea precursors and solvents used to prepare different PbSe nanocrystals. PbSe nanocrystals are synthesized by the route summarized at the top of the figure, producing nanocrystals that are characterized by absorbance spectroscopy (left) and TEM of selected samples (right. TEM of sample a is shown at top; TEM of sample d is shown at center; TEM of sample e is shown at bottom). Conditions used to prepare each sample are provided.

Figure 19:
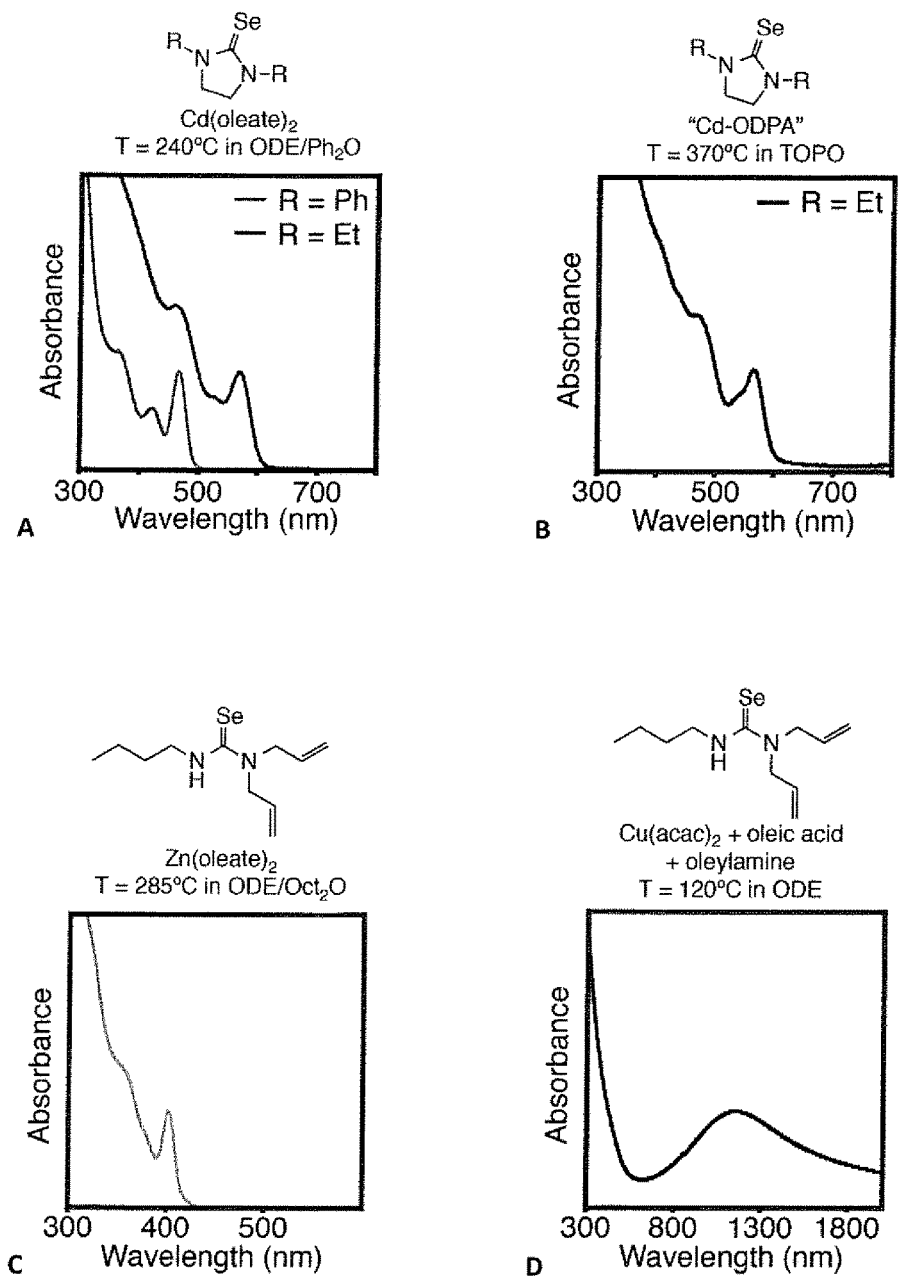
FIG. 19 presents absorbance spectra for CdSe, ZnSe, and $Cu_{2-x}Se$ nanocrystals prepared from the selenourea precursors shown in accordance with certain embodiments of the present disclosure.

Choice of the selenium precursor compound can provide control over nanocrystal formation rate. In certain embodiments, slower-reacting tetrasubstituted selenoureas can provide we are able to synthesize high-quality zinc blende and wurtzite CdSe nanocrystals at high temperatures, as shown in FIG. 19. FIG. 19A presents an absorbance spectrum for zinc blende CdSe nanocrystals. In certain embodiments, selenium precursor compounds with electron-deficient phenyl substituents can lead to faster precursor conversion and smaller final zinc blende CdSe nanocrystal size than selenium precursor compounds with more electron-rich ethyl substituents, as shown in FIG. 19A. FIG. 19B presents an absorbance spectrum for wurtzite CdSe nanocrystals. In certain embodiments, ZnSe and $Cu_{2-x}Se$ nanocrystals can be prepared from selenium precursor compounds. FIG. 19C presents an absorbance spectrum for ZnSe nanocrystals. FIG. 19D presents an absorbance spectrum for $Cu_{2-x}Se$ nanocrystals. Trisubstituted selenoureas can react with zinc oleate at 285° C. to form ZnSe nanocrystals.

In addition to the synthesis of thioureas discussed herein, isothiocyanates can react with other classes of molecules to extend the library of sulfur-delivering precursors. As shown in Scheme 7, for example and without limitation, isothiocyanates can react with alcohols to form O-thiocarbamates or with thiols to form dithiocarbamates. Such reactions can take hours, but can be accelerated, for example, if an alkoxide is used. The use of (di)thiocarbamates and their metal salts can be considered as competent chalcogenide precursors for nanocrystal synthesis previously. Furthermore, according to the techniques of the disclosed subject matter, synthesis of (di)thiocarbamates and their metal salts from isothiocyanates can be used to create a library of precursors with variable reactivity. Additionally or alternatively, primary and secondary phosphines and phosphine oxides can react with isothiocyanates to form the analogous molecule. In addition, in the exemplary embodiments herein, isothiocyanates can react with nucleophilic molecules containing a heteroatom-hydrogen bond to add across the C=N bond.

Scheme 7: Exemplary Isothiocyanate Reactions

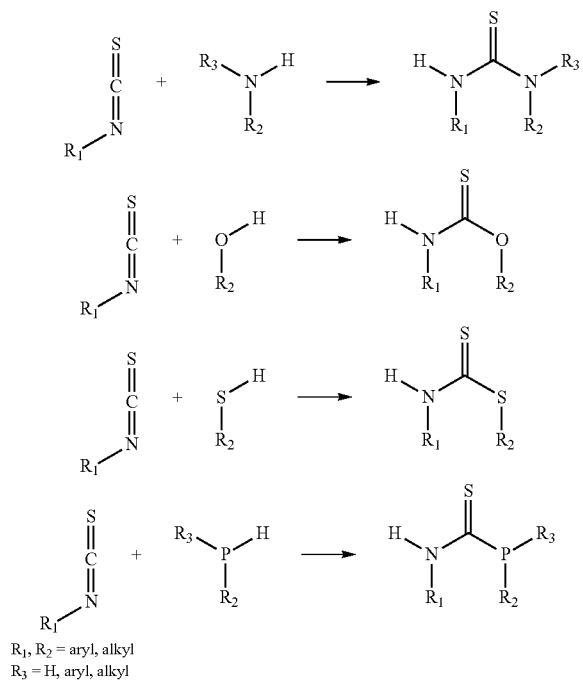

R$_1$, R$_2$ = aryl, alkyl
R$_3$ = H, aryl, alkyl

Without being bound to any particular theory, it is possible that mono-, di-, and trisubstituted thioureas can react with metal salts to form metal complex intermediates that include a metal-sulfur bond, as presented in Scheme 8.

Scheme 8. Reaction of Thiourea and Metal Salt to Provide Metal Complex

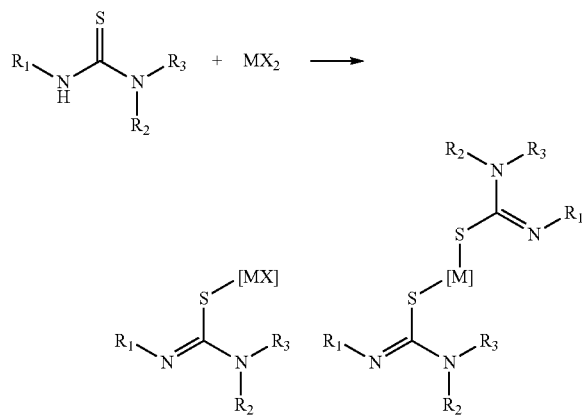

Intermediates.
Metal complex intermediates can react further to provide metal sulfide nanocrystals. In certain embodiments, metal complex intermediates (e.g., species containing metal-sulfur or metal-selenium bonds) could themselves be used as precursor compounds to general metal chalcogenide nanocrystals.

By way of non-limiting example, sulfur-containing precursor compounds (sulfur precursors) of the presently disclosed subject matter can include the following compounds: 1-(4-cyanophenyl)-3-(4-octylphenyl)thiourea, 1-(4-methoxyphenyl)-3-(4-octylphenyl)thiourea, 1-(4-octylphenyl)-3-phenylthiourea, 1-(4-cyanophenyl)-3-dodecylthiourea, 1-dodecyl-3 (4-methoxyphenyl)thiourea, 1-dodecyl-3-phenylthiourea, 1-cyclopentyl-3-dodecylthiourea, 1-cyclopropyl-3-dodecylthiourea, 1-sec-butyl-3-dodecylthiourea, 1-isobutyl-3-dodecylthiourea, 1-butyl-3-dodecylthiourea, 1-allyl-3-dodecylthiourea, 1-(4-chlorophenyl)-3-dodecylthiourea, 1-(2,3-dichlorophenyl)-3-dodecylthiourea, 1-tert-butyl-3-dodecylthiourea, 1-dodecyl-3-(4-fluorophenyl)thiourea, 1-dodecyl-3-(4-trifluoromethylphenyl)thiourea, 1-dodecyl-3-(4-nitrophenyl)thiourea, 1-dodecyl-3-(4-methylphenyl)thiourea, 1-dodecyl-3-(2-methallyl)thiourea, 1-dodecyl-3-hexylthiourea, 1-dodecyl-3-isopropylthiourea, 1-dodecyl-3-(2-methoxyphenyl)thiourea, 1-dodecyl-3-cyclohexylthiourea, 1-dodecyl-3-benzylthiourea, 1,3-diphenylthiourea, 1-butyl-3-phenylthiourea, 1-(2,3-dichlorophenyl)-3-phenylthiourea, 1-tert-butyl-3-phenylthiourea, bis(trifluoromethyl)phenyl)-3-phenylthiourea, 1-(2-methylphenyl)-3-phenylthiourea, 1-(4-trifluoromethylphenyl)-3-phenylthiourea, 1-(4-methylphenyl)-3-phenylthiourea, 1-(2-methallyl)-3-phenylthiourea, 1-hexyl-3-phenylthiourea, 1-isopropyl-3-phenylthiourea, 1-(2-methoxyphenyl)-3-phenylthiourea, 1-octyl-3-phenylthiourea, 1-cyclohexyl-3-phenylthiourea, 1-hexyl-3-(4-cyanophenyl)thiourea, 1-hexyl-3-(4-methoxyphenyl)thiourea, 1-hexyl-3-phenylthiourea, 1-hexyl-3-(4-chlorophenyl)thiourea, 1-hexyl-3-(4-fluorophenyl)thiourea, 1-hexyl-3-(4-trifluoromethylphenyl)thiourea, 1-hexyl-3-(4-nitrophenyl)thiourea, 1-hexyl-3-hexylthiourea, 1-(4-cyanophenyl)-3-(2-ethylhexyl)thiourea, 1-phenyl-3-(2-ethylhexyl)thiourea, 1-allyl-3-(2-ethylhexyl)thiourea, 1-butyl-3-phenylthiourea, 1,3-dicyclohexylthiourea, 1,3-diisopropylthiourea, 3-phenyl-1,1-dioctylthiourea, 3-hexyl-1,1-dioctylthiourea, 1,1-dibutyl-3-phenylthiourea, 1,1-dibutyl-3-hexylthiourea, 1,3-diallylthiourea, imidazolidine-2-thione, and tetramethylthiourea.

By way of non-limiting example, selenium-containing precursor compounds (selenium precursors) of the presently disclosed subject matter can include the following compounds: 1-butyl-3,3-dimethylselenourea, 1-butyl-3,3-dipropylselenourea, 1-butyl-3-dodecylselenourea, 1,1,3-tributylselenourea, 1-butyl-3-cyclohexylselenourea, 1,1-diallyl-3-butylselenourea, 1-butyl-3-butylselenourea,1,3-dibutyl-1-methylselenourea,1,1-dibenzyl-3-butylselenourea, 1-cyclohexyl-3,3-dimethylselenourea, 1-cyclohexyl-3,3-dipropylselenourea, 1-cyclohexyl-3-dodecylselenourea, 1,1-dibutyl-3-cyclohexylselenourea, 1,3-dicyclohexylselenourea, 1,1-diallyl-3-cyclohexylselenourea, 1-butyl-3-cyclohexylselenourea, 1-tert-butyl-3,3-dimethylselenourea, 1,3-diethylimidazolidine-2-selenone, 1,3-diphenylimidazolidine-2-selenone, 1,3,4,5-tetramethylimidazoline-2-selenone, 1,3-diisopropylimidazoline-2-selenone, tetrabenzylselenourea, and tetracyclohexylselenourea.

As described above and in the Examples, the presently disclosed subject matter provides, inter alia, a library of inexpensive and air-stable substituted thioureas of formula (I) whose conversion to metal sulfide nanocrystals can be finely tuned by adjusting their organic substituents. Thioureas can be obtained in quantitative or near-quantitative yields via a "click reaction" between commercially available substituted isothiocyanates and primary or secondary amines. The electrophilicity of isothiocyanates makes the reaction with amines rapid at room temperature, allowing a large variety of structures to be prepared including N,N'-diaryl, as well as bulky N,N,N'-trialkylthiourea structures. While isothiocyanates are formed in quantitative yields, and can be used directly in a nanocrystals synthesis, many are readily purified by recrystallization providing access to analytically pure, air-stable materials in multigram quantities.

As described above and in the Examples, the presently disclosed subject matter provides, inter alia, metal sulfide, metal selenide, and mixed metal sulfide/metal selenide nanocrystals. An advantage of the compositions and methods of the present disclosure can be that preparation of such nanocrystals from reaction of a sulfur- and/or selenium-containing precursor compound with a metal salt can be conducted in a low boiling solvent such as 1-octene, dibutyl ether, or a mixture thereof. Such solvents can be conveniently removed under vacuum. Removal of reaction solvent by vacuum can substantially reduce the amount of solvent necessary to clean and isolate nanocrystals to a well-defined ligand coverage.

The nanocrystals of the present disclosure can have numerous applications. For example, the nanocrystals can be used as quantum dots in optical applications. By way of non-limiting example, the nanocrystals of the present disclosure can be used in computing, in biology (e.g., as dyes, indicators, imaging agents, and/or sensors), photovoltaic devices, light emitting devices, and photodetector devices. The nanocrystals of the present disclosure can be used in various electronic applications (e.g., in screens for televisions or other consumer electronics).

EXAMPLES

Materials and Methods. All manipulations were performed in air unless otherwise indicated. Toluene (99.5%), tetrachloroethylene (99%), methyl acetate (99%), hexane (98.5%), methanol (99.8%), acetonitrile (99.5%), diphenyl ether (99%), 1-octadecene (90%), cadmium nitrate tetrahydrate (98%), sodium hydroxide (97%, 98%), oleic acid (99%), dodecylamine (98%), phenyl isothiocyanate (98%), 4-chlorophenyl isothiocyanate (99%), hexyl isothiocyanate (95%), cyclohexyl isothiocyanate (98%), 4-nitrophenyl isothiocyanate (98%), 4-methoxyphenyl isothiocyanate (98%), isopropyl isothiocyanate (97%), 4-(trifluoromethyl)phenyl isothiocyanate (97%), 4-cyanophenyl isothiocyanate (98%), hexylamine (99%), aniline (99%), dibutylamine (99.5%), N-butylmethylamine (96%), dimethylamine (2.0 M in THF), diallylamine (99%), triethyl orthoformate (98%), selenium (~100 mesh, 99.99%), benzonitrile (puriss., ≥99.0%), and γ-butyrolactone (≥99%) were obtained from Sigma Aldrich and used without further purification. Hexadecane (99%) was obtained from Sigma Aldrich, stirred over calcium hydride overnight, and distilled prior to use. Cyclohexyl isocyanide (98+%) and butyl isocyanide (98-99%) were obtained from Acros Organics and used without further purification. Zinc nitrate hexahydrate (99%), N,N'dianilinoethane (98+%) and N,N'-diethylethylenediamine (96%) were obtained from Alfa Aesar and used without further purification. Trioctylphosphine oxide (99%) was obtained from Sigma Aldrich and recrystallized three times from hot acetonitrile prior to use. Cadmium oxide (99.99%) was obtained from Strem Chemicals and used without further purification. Diphenyl ether (99%), dioctyl ether (99%), 1-octadecene (90%), hexadecane (99%) and octane (anhydrous, 99%) were obtained from Sigma Aldrich, stirred with calcium hydride overnight, distilled and stored in a glove box over 3 Å molecular sieves prior to use. 1-Octene (99%) was obtained from Acros Organics, stirred with calcium hydride overnight, distilled and stored in a glove box over 3 Å molecular sieves prior to use. Dibutyl ether (anhydrous, 99.3%), diethylene glycol dimethyl ether (anhydrous, 99.5%), and anisole (anhydrous, 99.7%), were obtained from Sigma Aldrich, brought into a glove box, shaken with activated alumina, filtered, and stored over 3 Å molecular sieves prior to use.

Kinetics experiments were monitored at 400 nm using an Ocean Optics TP300 dip probe (2 mm path length) attached to a Perkin-Elmer Lambda 650 spectrophotometer equipped with deuterium and halogen lamps (resolution=1.7 $s^{-1}$, slit width=5 nm). Full UV-Vis-NIR spectra were obtained using a Perkin-Elmer Lambda 950 spectrophotometer equipped with deuterium and halogen lamps and a PbS detector. Fluorescence measurements were performed using a Fluoromax 4 from Horiba Scientific, and quantum yields were determined using a quanta-phi integrating sphere attachment. Samples for UV-Vis-NIR and fluorescence were dissolved in tetrachloroethylene, and a blank with the same solvent concentrations as the corresponding sample was used. Transmission electron micrographs were obtained on a JEOL 2100F TEM. Powder XRD analysis was performed on a Scintag X-ray diffractometer. NMR spectroscopy was performed on Bruker 300, 400, and 500 MHz spectrometers. $^{77}$Se NMR spectra were externally referenced to a solution of diphenyl diselenide in $C_6D_6$ at 464.10 ppm.

Example 1

Precursor Synthesis

Example 1(a)

Synthesis of zinc oleate ($Zn(oleate)_2$)

9.54 mmol (0.382 g) sodium hydroxide was dissolved in 90 mL methanol. 9.54 mmol (2.694 g) of oleic acid was added and the solution was stirred for five minutes. A solution of 3.18 mmol (0.947 g) zinc nitrate hexahydrate was prepared in 15 mL methanol and added dropwise, with the formation of a white precipitate. After the addition, the white solid was collected by vacuum filtration, washed with excess methanol, and dried under vacuum for two days prior to storage in a glove box.

Example 1(b)

Synthesis of lead oleate ($Pb(oleate)_2$)

Using conventional methods, 90 mmol of sodium hydroxide are dissolved in 2 L of methanol. Once dissolved, 90 mmol of oleic acid is added and stirred for ~5 minutes. 40 mmol of $Pb(NO_3)_3$ is then added with 500 mL more methanol, and the whole solution heated until everything is soluble. Once a clear solution is obtained, the heat and stirring are turned off. Once close to room temperature, the still-clear solution is decanted into a new flask away from any insoluble residue. The new flask is stored in a freezer overnight and the $Pb(ole)_2$ is allowed to precipitate. The resulting white powder is filtered, washed with cold methanol, and then dried at reduced pressure for >6 hours. The Pb(ole)$_2$ is stored in a nitrogen-filled glovebox until ready for use, due to the slow development of yellow color upon exposure to air.

Example 1(c)

Synthesis of lead oleate (Pb(oleate)$_2$)

Using conventional methods, 45 mmol (1.800 g) of sodium hydroxide was dissolved in 1 L of methanol as it began to heat. Once dissolved, 45 mmol (12.710 g) of oleic acid was slowly added and stirred for ~5 minutes. 20 mmol (6.624 g) of Pb(NO$_3$)$_2$ was then added with 250 mL more methanol, and the whole solution was heated until everything dissolved. Once a clear solution was obtained, heat and stirring were turned off. After cooling to room temperature, the solution was decanted into a new flask away from any insoluble residue. The new flask is stored in a 5° C. refrigerator overnight in order to precipitate the Pb(ole)$_2$. The resulting white powder was filtered, washed with cold methanol, and then dried at reduced pressure for >6 hours. The Pb(ole)$_2$ was stored in a nitrogen-filled glovebox until use to avoid decomposition in air. This reaction could also be run at double the scale described with no observable changes. Isolated yields were in the range of 30-60%.

Example 1(d)

Synthesis of Lead Oleate (Pb(Oleate)$_2$) from Lead Trifluoroacetate (Pb(O$_2$CCF$_3$)$_2$ Lead (II) oxide (30.00 g, 134.4 mmol) was added to a round bottom flask. With stirring trifluoroacetic acid (51.4 mL, 672.0 mmol, 5 equiv) was slowly added, followed by trifluoroacetic anhydride (38.0 mL, 268.8 mmol, 2 equiv). The mixture was stirred until a clear, colorless solution was obtained. The volatiles were then removed under vacuum leaving a white solid. The flask was opened and 600 mL ethanol was added. The mixture was stirred to obtain a clear, colorless solution. Oleic acid (79.727 g, 282.3 mmol, 2.1 equiv) was added with stirring, followed by dropwise addition of triethylamine (28.562 g, 282.3 mmol, 2.1 equiv). This solution was stirred at room temperature for two hours and then stored in a freezer overnight causing a white precipitate to form. The powder was collected by vacuum filtration, washed with methanol, and then dried under vacuum. $^1$H NMR (C$_6$D$_6$, 500 MHz) δ=5.56 (m, 4H, =CH—), 2.53 (t, $^3$J$_{H-H}$=7.7 Hz, 4H, COCH$_2$), 2.19 (m, 8H, =CHC$\underline{H}$$_2$), 1.89 (m, 4H, COCH$_2$C$\underline{H}$$_2$), 1.58-1.27 (m, 40H, (CH$_2$)$_6$ and (CH$_2$)$_4$), 0.95 (t, $^3$J$_{H-H}$=6.8 Hz,6H); $^{13}$C NMR (C$_6$D$_6$, 125 MHz) δ=184.05 (OOC), 138.90 (=CH—), 136.86 (=CH—), 39.87, 32.43 (CO$\underline{C}$H$_2$), 30.57 (CH$_2$), 30.38 (CH$_2$), 30.33 (CH$_2$), 30.14 (CH$_2$), 30.12 (CH$_2$), 29.91 (CH$_2$), 29.89 (CH$_2$), 27.95 (=CH$\underline{C}$H$_2$—), 27.86 (=CH $\underline{C}$H$_2$—), 26.29 (COCH$_2$$\underline{C}$H$_2$), 23.20 ($\underline{C}$H$_2$CH$_3$), 14.43 (CH$_3$); Anal. Calcd. For PbO$_4$C$_{36}$H$_{66}$: C, 56.15; H, 8.64; O, 8.31.

Example 1(e)

Synthesis of N,N' disubstituted thioureas

A solution of alkylamine (3.0 mmol) in toluene (2.5 mL) was added to a solution of alkyl or aryl isothiocyanate (3.0 mmol) in toluene (2.5 mL). The resulting liquid was pumped under vacuum while stirring for 60 minutes to remove toluene, producing a powder. To produce thiourea crystals suitable for X-ray crystallography, the powder was dissolved in ~10 mL of diethyl ether or toluene and allowed to evaporate. For N,N'-diphenyl-thiourea, the volume of toluene was increased to 5 mL for each, resulting in 10 mL total.

Example 1(f)

Synthesis of N,N,N'-trialkylselenoureas

To a suspension of selenium (1.5 mmol) in tetrahydrofuran (1 mL) was added dialkylamine (1.5 mmol) and alkyl isocyanide (1.5 mmol). The reaction mixture was heated to reflux for 4 hours, passed through a syringe filter (PTFE, 0.2 μm pore size), and then pumped to dryness over 3 hours. If a nonvolatile amine or isocyanide (BP>140° C.) was used, the resulting powder was washed briefly with cold hexanes. The procedure could also be carried out in a nitrogen-filled glove box at room temperature over 24 hours. The selenourea product was stored in a glove box to prevent gradual decomposition in ambient conditions.

(C$_4$H$_9$)$_2$NC(Se)NHC$_6$H$_{11}$ (N,N-dibutyl-N'-cyclohexylselenourea)

Yield: 436.2 mg (91.6%). $^1$H NMR (C$_6$D$_6$, 400 Hz): δ=5.27 (d, $^3$J$_{H-H}$=7.2 Hz, 1H, —NH—), 4.85 (m, 1H, α-CH), 3.44 (t, $^3$J$_{H-H}$7.4 Hz, 4H, α—CH$_2$), 2.16 (m, 2H, 4-CH$_2$), 1.57-1.40 (m, 7H, (CH$_2$)$_2$ and 2,3,5,6-CH$_2$), 1.35-1.23 (m, 2H, (CH$_2$)$_2$ and 2,3,5,6-CH$_2$), 1.21-0.95 (m, 3H, (CH$_2$)$_2$ and 2,3,5,6-CH$_2$), 1.16 (q, $^3$J$_{H-H}$=7.4 Hz, 4H, —C$\underline{H}$$_2$CH$_3$), 0.83 (t, $^3$J$_{H-H}$=7.6 Hz, 6H, —CH$_3$); $^{13}$C {$^1$H} (100 MHz, C$_6$D$_6$): δ=180.03 ($^2$J$_{C-Se}$=217.6 Hz, C=Se), 56.88 (α-CH), 52.20 (α-CH$_2$), 33.43 (2-CH$_2$), 29.87 (NCH$_2$$\underline{C}$H$_2$), 25.93 (4-CH$_2$), 25.30 (3-CH$_2$), 20.47 ($\underline{C}$H$_2$CH$_3$), 14.12 (CH$_3$); $^{77}$Se {$^1$H} (C$_6$D$_6$, 76.3 MHz): δ=206.31; Anal. Calcd for C$_{15}$H$_{30}$N$_2$Se: C, 56.77; H, 9.53; N, 8.83. Found: C, 56.89; H, 9.21; N, 8.89; MS (FAB) m/z Calcd for [C$_{15}$H$_{30}$N$_2$$^{80}$Se+H$^+$]: 319.17. Found: 319.25.

(H$_2$C=CHCH$_2$)$_2$NC(Se)NHC$_6$H$_{11}$ (N,N-diallyl-N'-cyclohexylselenourea)

Yield: 2.1983 g (77.0%, 10 mmol scale). $^1$H NMR (C$_6$D$_6$, 400 Hz): δ=5.57 (m, 2H, —CH=), 5.38 (d, $^3$J$_{H-H}$=7.4 Hz, 1H, —NH—), 4.91 (m, 1H, =CH$_2$), 4.87 (m, 1H, =CH$_2$), 4.85-4.75 (m, 1H, α-CH—), 4.04 (d, $^3$J$_{H-H}$=2.9 Hz, 4H, N—CH$_2$—), 2.10 (m, 2H, 4-CH$_2$), 1.52-1.43 (m, 3H, 2,3,5,6-(CH$_2$)$_2$), 1.43-1.33 (m, 1H, 2,3,5,6-(CH$_2$)$_2$), 1.31-1.20 (m, 2H, 2,3,5,6-(CH$_2$)$_2$), 1.05-0.96 (m, 3H, 2,3,5,6-(CH$_2$)$_2$); $^{13}$C {$^1$H} (100 MHz, C$_6$D$_6$): δ=181.74 ($^2$J$_{C-Se}$=218.8 Hz, C=Se), 133.05 (—CH=), 117.44 (=CH$_2$), 57.10 (α-CH$_2$), 54.79 (α-CH), 33.13 (2-CH$_2$), 25.88 (4-CH$_2$), 25.10 (3-CH$_2$); $^{77}$Se {$^1$H} (C$_6$D$_6$, 76.3 MHz): δ=217.25; Anal. Calcd for C$_{15}$H$_{30}$N$_2$Se: C, 54.73; H, 7.77; N, 9.82. Found: C, 55.00; H, 7.88; N, 9.74. MS (FAB) m/z Calcd for [C$_{15}$H$_{30}$N$_2$$^{80}$Se+H$^+$]: 287.10. Found: 287.19.

C$_4$H$_9$HNC(Se)N(C$_4$H$_9$)$_2$ (N,N,N'-tributylselenourea)

Yield: 2.8560 g (98.0%, 10 mmol scale). $^1$H NMR (C$_6$D$_6$, 400 Hz): δ=5.26 (br t, 1H, NH), 3.82 (td, $^3$J$_{H-H}$=7.3, 5.3 Hz, 2H, —NHC$\underline{H}$$_2$), 3.40 (t, $^3$J$_{H-H}$=7.8 Hz, 4H, NCH$_2$), 1.51-1.36 (m, 6H, β-CH$_2$), 1.21 (tq, $^3$J$_{H-H}$=7.5, 7.3 Hz, 2H, C$\underline{H}$$_2$CH$_3$), 1.13 (tq, $^3$J$_{H-H}$=7.6, 7.3 Hz, 4H, C$\underline{H}$$_2$CH$_3$), 0.83 (t, $^3$J$_{H-H}$=7.4 Hz, 3H, CH$_3$), 0.82 (t, $^3$J$_{H-H}$=7.4 Hz, 6H, CH$_3$); $^{13}$C {$^1$H} (100 MHz, C$_6$D$_6$): δ=181.84 ($^2$J$_{C-Se}$ 217.87 Hz, C=Se), 52.19 (NHCH$_2$), 48.64 (NCH$_2$), 31.94 (β-CH$_2$), 29.80 (β-CH$_2$), 20.47 ($\underline{C}$H$_2$CH$_3$), 20.43 ($\underline{C}$H$_2$CH$_3$), 14.06 (CH$_3$); $^{77}$Se {$^1$H} (C$_6$D$_6$, 76.3 MHz): δ=209.97; Anal. Calcd for C$_{13}$H$_{28}$N$_2$Se: C, 53.59; H, 9.69; N, 9.62. Found: C, 53.83; H, 9.44; N, 9.55. MS (FAB) m/z Calcd for [C$_{13}$H$_{28}$N$_2$$^{80}$Se+H$^+$]: 293.15. Found: 293.22.

($H_2C$=$CHCH_2$)$_2$NC(Se)NHC$_4$H$_9$ (N,N-diallyl-N'-butylselenourea)

Yield: 777.75 mg (93.8%, 3 mmol scale). $^1$H NMR (C$_6$D$_6$, 400 Hz): δ=5.54 (in, 2H, —CH=), 5.33 (br s, 1H, —NH—), 4.90-4.83 (m, 2H, =CH$_2$), 4.88-4.86 (m, 2H, =CH$_2$), 4.00 (br d, 4H, NCH$_2$—), 3.75 (td, $^3J_{H-H}$=7.2, 5.2 Hz, 4H, NHCH$_2$), 1.42-1.34 (m, 2H, β-CH$_2$), 1.52-1.43 (qt, $^3J_{H-H}$=7.5, 7.3, Hz, 2H, CH$_2$CH$_3$), 0.79 (t, $^3J_{H-H}$=7.3 Hz, 3H, CH$_3$); $^{13}$C {$^1$H} (100 MHz, C$_6$D$_6$): δ=183.47 ($^2J_{C-Se}$=219.1 Hz, C=Se), 132.94 (—CH=), 117.29 (=CH$_2$), 54.65 (NHCH$_2$), 54.79 (NCH$_2$), 31.66 (β-CH$_2$), 20.37 (CH$_2$CH$_3$), 14.03 (CH$_3$); $^{77}$Se {$^1$H} (C$_6$D$_6$, 76.3 MHz): δ=216.81; MS (FAB) m/z Calcd for [C$_{11}$H$_{20}$N$_2^{80}$Se+H$^+$]: 261.09. Found: 261.19.

C$_4$H$_9$NHC(Se)N(CH$_3$)(C$_4$H$_9$) (N,N'-dibutyl-N-methylselenourea)

Yield: 337.1 g (90.2%). $^1$H NMR (C$_6$D$_6$, 400 Hz): δ=4.85 (br, 1H, NH), 3.75 (td, $^3J_{H-H}$=7.4, 5.3 Hz 2H, —NHCH$_2$), 3.62 (br t, $^3J_{H-H}$=7.6 Hz 2H, NCH$_2$), 2.34 (s, 3H, NCH$_3$), 1.45-1.34 (m, 4H, β-CH$_2$), 1.19 (tq, $^3J_{H-H}$=7.7, 7.4 Hz, 2H, CH$_2$CH$_3$), 1.13 (tq, $^3J_{H-H}$=7.7, 7.2 Hz, 2H, CH$_2$CH$_3$), 0.85 (t, $^3J_{H-H}$=7.4 Hz, 3H, CH$_3$); $^{13}$C {$^1$H} (125 MHz, C$_6$D$_6$): δ=182.12 ($^2J_{C-Se}$=217.43 Hz, C=Se) 55.51 (NCH$_2$), 48.62 (NHCH$_2$), 37.30 (NCH$_3$), 32.01 (β-CH$_2$), 29.77 (β-CH$_2$), 20.43 (CH$_2$CH$_3$), 20.25 (CH$_2$CH$_3$), 14.12 (CH$_3$), 14.11 (CH$_3$); $^{77}$Se {$^1$H} (C$_6$D$_6$, 57.2 MHz): δ=201.46; MS (FAB) m/z Calcd for [C$_{10}$H$_{22}$N$_2^{80}$Se+H$^+$]: 251.10. Found: 251.19.

C$_4$H$_9$NHC(Se)N(CH$_3$)$_2$ (N-butyl-N',N'-dimethylselenourea)

$^1$H NMR (C$_6$D$_6$, 400 Hz): δ=5.10 (br, 1H, NH), 3.74 (m, 2H, —NHCH$_2$), 2.66 (s, 6H, NCH$_3$), 1.51-1.42 (m, 2H, β-CH$_2$), 1.21 (m, 2H, CH$_2$CH$_3$), 0.85 (t, $^3J_{H-H}$=7.4 Hz, 3H, CH$_3$); $^{13}$C {$^1$H} (125 MHz, C$_6$D$_6$): δ=182.59 ($^2J_{C-Se}$=217.19 Hz, C=Se), 48.69 (NCH$_3$), 41.18 (NHCH$_2$), 31.98 (β-CH$_2$), 20.40 (CH$_2$CH$_3$), 14.11 (CH$_3$); $^{77}$Se {$^1$H} (C$_6$D$_6$, 57.2 MHz): δ=212.52; MS (FAB) m/z Calcd for [C$_7$H$_{16}$N$_2^{80}$Se+H$^+$]: 209.06. Found: 209.13.

Example 1(g)

Synthesis of 2-selenoimidazolidines

Selenium (97.5 mmol), triethyl orthoformate (195 mmol), and amine or diamine (195 or 97.5 mmol, respectively) were added to a round bottom flask equipped with a reflux condenser and distillation apparatus. The reaction mixture was degassed by the freeze-pump-thaw method and then heated to 180° C. under argon with vigorous stirring for 8 hours. Over this period, the selenium dissolved and a liquid condensed in the receiving flask. The reaction mixture was then allowed to cool to room temperature and the reaction apparatus was opened to air. The reaction mixture was thrice shaken with activated carbon and filtered to remove colored impurities, using toluene or acetone to rinse the filter. The solution was dried under vacuum overnight and the resulting solid was stored in a nitrogen-filled glove box. It could be recrystallized by addition of pentane to a saturated solution in dichloromethane or toluene.

1,3-diethyl-2-selenoimidazolidine

Yield: 15.3 g (76.5%). $^1$H NMR (C$_6$D$_6$, 400 Hz): δ=3.58 (q, $^3J_{H-H}$=7.2 Hz, 4H, —CH$_2$—), 2.48 (s, 4H, —CH$_2$CH$_2$—), 0.88 (t, $^3J_{H-H}$=7.2 Hz, 6H, —CH$_3$); $^{13}$C {$^1$H} (100 MHz, C$_6$D$_6$): δ=180.95 ($^2J_{C-Se}$=223.3 Hz, C=Se), 46.15 (—CH$_2$—), 43.94 (—CH$_2$CH$_2$—), 12.18 (—CH$_3$); $^{77}$Se {$^1$H} (C$_6$D$_6$, 76.3 MHz): δ=82.47; MS (FAB) m/z Calcd for [C$_7$H$_{14}$N$_2$Se+H$^+$]: 207.04. Found: 207.11.

1,3-diphenyl-2-selenoimidazolidine $^1$H NMR (CD$_2$Cl$_2$, 500 Hz): δ=7.57 (m, 4H, m-CH), 7.46 (m, 4H, o-CH), 7.34 (tt, $^3J_{H-H}$=7.4, 1.2 Hz, 2H, p-CH), 2.48 (s, 4H, —CH$_2$CH$_2$—), 4.14 (s, 4H, —CH$_2$CH$_2$—); $^{13}$C {$^1$H} (125 MHz, CD$_2$Cl$_2$): δ=180.73 ($^2J_{C-Se}$=227.5 Hz, C=Se), 141.81 (ipso-C), 128.91 (m-CH), 127.16 (p-CH), 126.67 (o-CH) 51.17 (—CH$_2$CH$_2$—); $^{77}$Se {$^1$H} (CD$_2$Cl$_2$, 76.3 MHz): δ=172.03; MS (FAB) m/z Calcd for [C$_{15}$H$_{14}$N$_2$Se+H$^+$]: 303.04. Found: 303.10.

Example 2

Nanocrystal Synthesis

Example 2(a)

Synthesis of Copper Sulfide Nanocrystals

Copper acetylacetonate (0.2616 g, 1 mmol), 1-octadecene (7.89 g, 10 mL), oleylamine (1.605 g, 6 mmol), and oleic acid (0.2825 g, 1 mmol) were combined in a vial and degassed for 30 minutes. The mixture was heated to 160° C., turning a dark blue color, and a solution of phenyl-hexyl thiourea (0.1182 g, 0.5 mmol) in diphenyl ether (~2 mL) was injected. After 15 minutes, the now dark brown sample was removed from heat and allowed to cool to room temperature. The nanocrystals were cleaned by precipitating in methyl acetate, centrifuging for 10 minutes at 7000 rpm, and redispersing in hexane. This was repeated twice more to fully clean the nanocrystals.

Example 2(b)

Large-Scale Synthesis of PbS Nanocrystals 53 mmol (40.815 g) of Pb(oleate)$_2$ and 220 mL 1-octadecene were loaded into a 500 mL 3-neck round bottom flask. After degassing for 30 minutes at 100 C using an oil bath, the vessel was put under an atmosphere of argon and brought to 120° C. 22 mmol of the desired thiourea was then mixed with 15 mL diphenyl ether in a vial, and the vial heated in the same oil bath as the reaction flask. After ~2 minutes, the thiourea solution was pulled into a syringe and quickly injected into the flask. The reaction was allowed to run for 20 minutes before the flask was removed from the hot oil bath and submerged in an oil bath at room temperature. Once below 55° C., the contents of the reaction were split between two 500 mL centrifuge buckets, and then ~100 mL of methyl acetate was added to each bucket to precipitate the nanocrystals. After centrifuging at 4000 rpm for 10 minutes, the solution was decanted and remaining nanocrystal residue re-dissolved in toluene. This was repeated three times to dissolve the nano crystals, and then absorbance and yield of the sample were measured.

Related kinetics experiments were performed. In a nitrogen-filled glovebox, 0.216 mmol (166 mg) of Pb(oleate)$_2$, 19 mL of hexadecane, and a stir bar were added to a three neck round bottom flask and the sealed with two septa and a Schlenk-line adapter. The flask was brought out of the box, attached to the Schlenk line, and one of the septa was replaced with a homemade adapter for the dip-probe. The flask was covered in foil, and then immersed in a silicon oil bath of the desired temperate. Meanwhile, 0.216 mmol of the desired thiourea and 1.25 g (1.2 mL at room temperature) was weighed into a vial. After at least 10 minutes to allow the flask to reach thermal equilibrium with the oil bath, the thiourea vial was also immersed in the oil bath for ~30 seconds. The UV-vis then began to measure the absorbance at 400 nm, and the thiourea vial was removed from the oil bath. A microliter syringe was used to measure 1 mL of stock thiourea solution (0.18 mmol thiourea), which was quickly injected into the flask. This resulted in 20 mL of total solution, with an initial Pb(oleate)$_2$ concentration of 10.8 mM and thiourea concentration of 9 mM. The reaction was run for 20 minutes after the injection occurred, at which time a 250 uL aliquot was removed to measure the full UV-Vis-NIR spectrum, and a 150 uL aliquot was removed for TEM. The UV-Vis-NIR aliquot was dissolved in 2.25 mL tetrachloroethylene, and the TEM aliquot was dissolved in 3 mL hexane. The kinetics data, an example of which is shown in FIG. 7, was corrected by doing a baseline correction to move the average absorbance prior to injection to 0 a.u., and doing a time correction to establish t=0 as the initial appearance of absorbance at 400 nm.

Example 2(e)

Synthesis of Cadmium Selenide/Cadmium Sulfide Core/Shell Nanocrystals 200 nmol of isolated wurtzite cadmium selenide nanocrystals dissolved in pentane were mixed with 1-octadecene (3.0 mL) and oleylamine (3.0 mL) in a 3-neck round bottom flask fitted with a glass thermocouple adapter, a rubber septum, and gas adapter. The sample was degassed under vacuum for 60 minutes to remove excess pentane, oxygen, and water. The sample was then heated to 210° C. using a heating mantle. Once at thermal equilibrium, cadmium oleate (130 mg, 0.193 mmol) and N-n-hexyl-N'-di-n-butyl thiourea (53 mg, 0.193 mmol), each dissolved in 4 mL of 1-octadecene, were separately injected into the CdSe-containing flask at a rate of 2 mL hr$^{-1}$. After two hours the precursors had been fully injected and the sample was allowed to anneal for an additional hour at 210° C. The sample was then cooled to room temperature, producing an orange/red solution. Quantum yield was determined by taking aliquots of the solution and dissolving in toluene.

Example 2(d)

Synthesis of Lead Sulfide Nanocrystals

Lead sulfide nanocrystals were synthesized according to the general procedure presented in the following scheme:

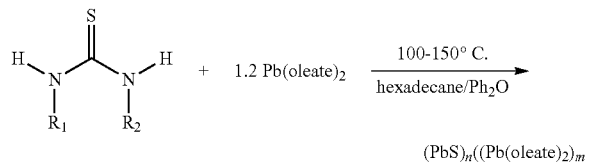

Six thiourea precursor compounds were studied, of the general formula N-(4-X-phenyl)-N'-dodecyl-thiourea. (In other words, the six thiourea precursor compounds were substituted such that R$_1$ was dodecyl and R$_2$ was a para-substituted aryl substituent where the para substituent X was variable and defined as follows.) For trial (a), X=CN and the reaction temperature was 120° C. For trial (b), X=CF$_3$ and the reaction temperature was 120° C. For trial (c), X=Cl and the reaction temperature was 120° C. For trial (d), X=OMe and the reaction temperature was 150° C. For trial (e), X=H and the reaction temperature was 120° C. For trial (f), X=OMe and the reaction temperature was 120° C.

Figure 20:
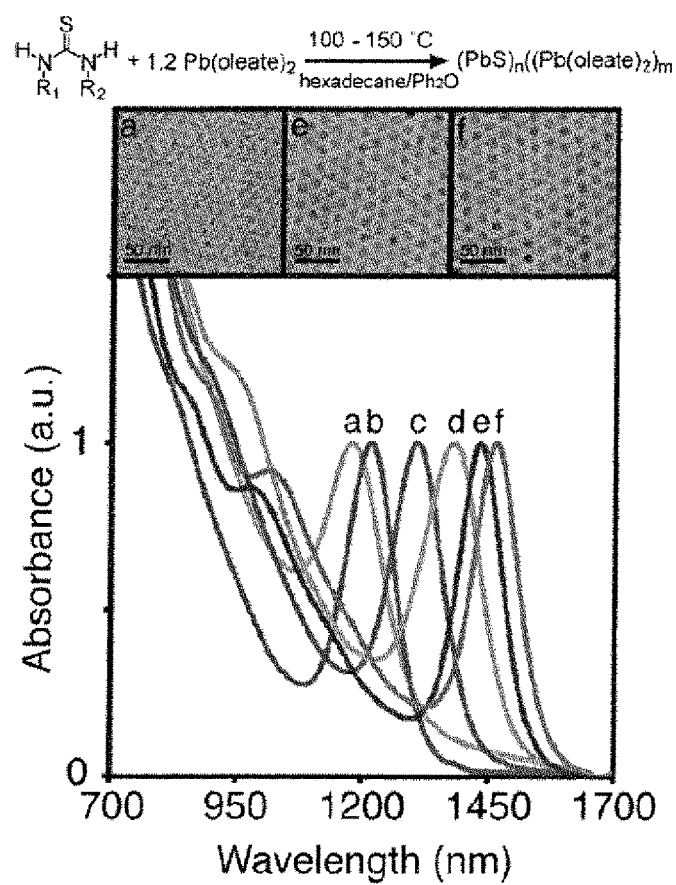
FIG. 20 presents TEM (transmission electron microscopy) and absorbance spectroscopy data characterizing a series of lead sulfide nanoparticles prepared from thiourea precursor compounds. Six thiourea precursor compounds were studied, of the general formula N-(4-X-phenyl)-N'-dodecyl-thiourea. For trial (a), X=CN and the reaction temperature was 120° C. For trial (b), X=CF3 and the reaction temperature was 120° C. For trial (c), X=Cl and the reaction temperature was 120° C. For trial (d), X=OMe and the reaction temperature was 150° C. For trial (e), X=H and the reaction temperature was 120° C. For trial (f), X=OMe and the reaction temperature was 120° C.

The resulting nanocrystals were characterized by TEM (Transmission electron microscopy) and absorbance spectroscopy. These results are presented in FIG. 20. As shown in FIG. 20, secondary N,N'-disubstituted thioureas a-f react readily with lead oleate, providing access to colloidal PbS nanocrystals at temperatures less than or equal to 150° C. UV-Vis-NIR absorption spectra of representative samples (FIG. 20) have sharp absorption features ((λ(1Se-1Sh)=900-2000 meV, FWHM=30-80 meV) characteristic of exceptionally narrow size distributions (σ≤8%, or +/−0.4 nm for ~5 nm diameter nanocrystals and +/−0.6 for ~7 nm diameter nanocrystals).

The kinetics of lead sulfide formation were studied by monitoring the nanocrystals absorbance in situ using a dip-probe. At λ=400 nm the absorbance is size independent and proportional to the concentration of lead sulfide formula units within nanocrystals. See generally Moreels et al. *ACS Nano* 2009, 3, 3023-3030. The kinetics experiments were conducted as follows.

In a nitrogen-filled glovebox, 0.216 mmol (166 mg) of Pb(oleate)$_2$, 19 mL of hexadecane, and a stir bar were added to a three neck round bottom flask and the sealed with two septa and a Schlenk-line adapter. The flask was brought out of the box, attached to the Schlenk line, and one of the septa was replaced with a homemade adapter for the dip-probe. The flask was covered in foil, and then immersed in a silicon oil bath of the desired temperate. Meanwhile, 0.216 mmol of the desired thiourea and 1.25 g (1.2 mL) diphenyl ether was weighed into a vial. After at least 10 minutes to allow the flask to reach thermal equilibrium with the oil bath, the thiourea vial was also immersed in the oil bath for ~30 seconds. The UV-vis then began to measure the absorbance at 400 nm, and the thiourea vial was removed from the oil bath. A microliter syringe was used to measure 1 mL of stock thiourea solution (0.18 mmol thiourea), which was quickly injected into the flask. This resulted in 20 mL of total solution, with an initial Pb(oleate)$_2$ concentration of 10.8 mM and thiourea concentration of 9 mM. The reaction was run for 20 minutes after the injection occurred, at which time a 250 uL aliquot was removed to measure the full UV-Vis-NIR spectrum, and a 150 uL aliquot was removed for TEM. The UV-Vis-NIR aliquot was dissolved in 2.25 mL tetrachloroethylene, and the TEM aliquot was dissolved in 3 mL hexane. The kinetics data was corrected by doing a baseline correction to move the average absorbance prior to injection to 0 a.u., and doing a time correction to establish t=0 as the initial appearance of absorbance at 400 nm.

Example kinetics traces are shown in FIG. 7. Quantitative formation of PbS occurred over a few minutes. The formation kinetics are well described by a single exponential, allowing pseudo-first-order rate constants ($k_{obs}$ (sec$^{-1}$)) to be extracted and the relative thiourea reactivity to be compared in a quantitative fashion ($k_{rel}$ (sec$^{-1}$)) (FIG. 3).

Example 2(e)

Large-Scale Synthesis of PbS Nanocrystals

In a glove box, 27.8 mmol (21.40 g) of Pb(oleate)2 and 220 mL 1-octene were loaded into a 500 mL 3-neck round bottom flask equipped with two rubber septa and a Teflon-sealable Straus adapter. The flask was sealed and transferred to a Schlenk line, where it was brought to 120° C. in an oil bath. While the temperature was stabilizing, 11 mL of anhydrous dibutyl ether, 23.2 mmol (2.77 mL) of phenyl isothiocyanate and 23.2 mmol (3.80 mL) of 2-ethylhexylamine were added to a 20 mL scintillation vial and stirred at 120° C. in a separate oil bath. Once the temperature of the Pb(oleate)2 solution stabilized at 120° C., the thiourea solution was pulled into two syringes and quickly injected into the flask. The reaction was allowed to run for 30 minutes before the flask was removed from the hot oil bath. Once cooled to ~35° C., the septa were replaced with glass stoppers under positive pressure of argon, and the solvent was removed in vacuo and collected in a liquid nitrogen-cooled pre-trap. Once the flask was near dryness, it was sealed and brought into a glove box. 30 mL of toluene was added, and the resulting slurry was split between two centrifuge tubes and centrifuged at 4000 rpm for 10 minutes. The nanocrystal solution was decanted and any solids were left behind. 30 mL of methyl acetate was added to the solution to precipitate the nanocrystals. After centrifuging at 4000 rpm for 10 minutes, the clear solution was decanted and the remaining nanocrystal residue re-dissolved in toluene. This was repeated five times to reach a ligand coverage of ~1.9 Pb(oleate)2 ligands per square nanometer as measured by absorbance and 1H NMR spectroscopy.

Example 2(f)

Synthesis and Isolation of PbSe Nanocrystals

In a glove box, 0.96 mmol (739.3 mg) of Pb(oleate)$_2$ and 38 mL 1-octene were loaded into a 100 mL 3-neck round bottom flask equipped with two rubber septa and a Teflon-sealable Straus adapter. 0.80 mmol (253.9 mg for N-cyclohexyl-N',N'-dibutylselenourea) of the selenourea was loaded into a scintillation vial with 2 mL of dibutyl ether and sealed with a rubber septum. The flask was sealed and connected to a Schlenk line, where it was brought to 100° C. in an oil bath. The vial was connected to the Schlenk line via needle adapter and heated to 100° C. Once the temperature of the Pb(oleate)$_2$ solution stabilized, the selenourea solution was quickly injected into the flask. The reaction was allowed to run for 30 minutes, taking aliquots and dispersing them in tetrachloroethylene if desired, before the flask was removed from the hot oil bath. Once cooled to ~35° C., the septa were replaced with glass stoppers under positive argon flow, and the solvent was removed in vacuo and collected in a liquid nitrogen-cooled pre-trap. Once the flask was near dryness, it was sealed and brought into a glove box. 6 mL of toluene was added and the resulting slurry was split between two centrifuge tubes and centrifuged at 7000 rpm for 5 minutes. The nanocrystal solution was decanted and any solids were left behind. 12 mL of methyl acetate was added to each solution to precipitate the nanocrystals. After centrifuging at 7000 rpm for 5 minutes, the clear solution was decanted and the remaining nanocrystal residue re-dissolved in toluene. This was repeated three times. The nanocrystals were then dried in vacuo, at which point yield and ligand coverage were measured.

Exemplary results are shown in FIG. 16. The size distribution of the nanocrystals was narrow ($\sigma$=10.0%). The 1H NMR spectrum of the 2.5 nm PbSe nanocrystals is presented at bottom. The PbSe nanocrystals were found to have a ligand coverage of 3.4±0.3 oleates/nm2, corresponding to a Pb:Se ratio of 1.24±0.1.

Example 2(g)

Synthesis and Isolation of Zinc Blende CdSe Nanocrystals

In a glove box, 0.12 mmol (81.04 mg) of Cd(oleate)$_2$ and 9.5 mL 1-octadecene were loaded into a 3-neck round bottom flask equipped with a stir bar, Schlenk adapter, thermocouple adapter, and rubber septum. 0.10 mmol of the selected selenourea and 0.5 mL diphenyl ether were loaded into a 4 mL scintillation vial and tightly capped with a rubber septum. Both were attached to a Schlenk line and the Cd(oleate)$_2$ mixture was heated to 240° C. Once the flask neared 240° C., the vial containing the selenourea was heated with a heat gun until the contents were homogenous, and once the flask reached 240° C., the selenourea was rapidly injected. The reaction was allowed to run for an appropriate length of time (2.5 minutes for 1,3-diphenyl-2-selenoimidazolidine; 45 minutes for 1,3-diethyl-2-selenoimidazolidine), taking aliquots and dispersing them in toluene if desired. The reaction was allowed to cool and the mixture was transferred to a glove box. The nanocrystal solution was precipitated with methyl acetate and centrifuged at 7000 rpm for 10 minutes. The supernatant was discarded and the nanocrystal residue redissolved in a minimum amount of toluene. The nanocrystals were precipitated with methyl acetate twice more and dried in vacua, at which point yield and ligand coverage were measured.

Example 2(h)

Synthesis of Wurtzite CdSe Nanocrystals 0.12 mmol (15.41 mg) of cadmium oxide, 0.216 mmol (72.25 mg) oetadecylphosphonic acid, and 9.5 g trioctylphosphine oxide were added to a 3-neck round bottom flask equipped with a reflux condenser, thermocouple adapter, rubber septum, and stir bar. This mixture was heated to 100° C. and degassed in vacuo (~60 mtorr) for 1 hour. During this time, 0.10 mmol of the desired selenourea and 0.5 g trioctylphosphine oxide were weighed into a 4-mL scintillation vial in a glove box, tightly sealed with a rubber septum, and attached to a Schlenk line. After degassing, the cadmium oxide suspension was placed under argon and heated to 370° C. The red color gradually disappeared, giving a pale yellow solution. At this point, the selenourea mixture was heated to 100° C. until homogenous and rapidly injected into the 3-neck flask. The reaction was allowed to run for an appropriate length of time (15 minutes for 1,3-diethyl-2-selenoimidazolidine), taking aliquots and dispersing them in toluene if desired.

Example 2(i)

Synthesis of ZnSe Nanoerystals

In a glove box, 0.12 mmol (75.40 mg) of Zn(oleate)$_2$ and 9.5 mL 1-octadecene were loaded into a 3-neck round bottom flask equipped with a stir bar, Schlenk adapter, thermocouple adapter, and rubber septum. 0.10 mmol of the selected selenourea and 0.5 mL dioctyl ether were loaded into a 4 mL scintillation vial and tightly capped with a rubber septum. Both were attached to a Schlenk line and the Cd(oleate)$_2$ mixture was heated to 285° C. Once the flask neared 285° C., the vial containing the selenourea was heated with a heat gun until the contents were homogenous, and once the flask reached 285° C., the selenourea was rapidly injected. The reaction was allowed to run for an appropriate length of time (2.5 min for N,N-diallyl-N-n-butyl-selenourea), taking aliquots and dispersing them in hexane if desired.

Example 3

Size Distribution Analysis

Size distribution analysis could be performed using the formula provided by Moreels et al. (Chem. Mater. 2007, 19,

What is claimed is:

1. A process for preparing nanocrystals, comprising:
   (a) contacting a metal salt in an organic solvent solution with a precursor compound selected from the group consisting of sulfur compounds of Formulae (I)-(IV) and selenium compounds of Formulae (V) and (VI) at a temperature in a range of from about 80° C. to about 370° C. to form a suspension of monodispersed nanocrystals having median particle size and a particle size distribution characterized by a standard deviation, such that the standard deviation ($\sigma$) of the particle size distribution is less than or equal to 13% of the median particle size of the nanocrystals, and
   (b) collecting the nanocrystals from suspension;
   wherein
   Formula (I) has the structure:

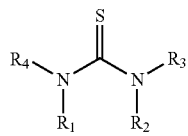

(I)

wherein $R_1$, $R_2$, and $R_3$ are independently selected from the group consisting of H, substituted or unsubstituted alkyl, substituted or unsubstituted cycloalkyl, substituted or unsubstituted alkenyl, substituted or unsubstituted cycloalkenyl, or substituted or unsubstituted aryl;

$R_4$ is independently selected from the group consisting of substituted or unsubstituted alkyl, substituted or unsubstituted cycloalkyl, substituted or unsubstituted alkenyl, substituted or unsubstituted cycloalkenyl, or substituted or unsubstituted aryl;

Formula (II) has the structure:

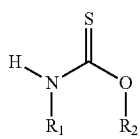

(II)

wherein $R_1$ and $R_2$ are independently selected from the group consisting of H, substituted or unsubstituted alkyl, substituted or unsubstituted cycloalkyl, substituted or unsubstituted alkenyl, substituted or unsubstituted cycloalkenyl, or substituted or unsubstituted aryl;

Formula (III) has the structure:

(III)

wherein $R_1$ and $R_2$ are independently selected from the group consisting of H, substituted or unsubstituted alkyl, substituted or unsubstituted cycloalkyl, substituted or unsubstituted alkenyl, substituted or unsubstituted cycloalkenyl, or substituted or unsubstituted aryl;

Formula (IV) has the structure:

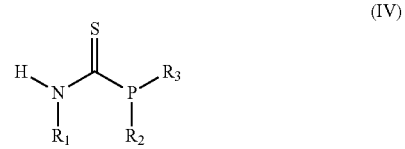

(IV)

wherein $R_1$, $R_2$, and $R_3$ are independently selected from the group consisting of H, substituted or unsubstituted alkyl, substituted or unsubstituted cycloalkyl, substituted or unsubstituted alkenyl, substituted or unsubstituted cycloalkenyl, or substituted or unsubstituted aryl;

Formula (V) has the structure:

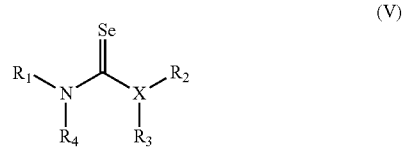

(V)

wherein $R_1$, $R_2$, $R_3$, and $R_4$ are independently selected from the group consisting of H, substituted or unsubstituted alkyl, substituted or unsubstituted alkenyl, substituted or unsubstituted cycloalkyl, substituted or unsubstituted cycloalkenyl, and substituted and unsubstituted aryl; and X is selected from the group consisting of N, O, S, Se, and P; and wherein $R_2$ is absent when X is O, S, or Se; and wherein $R_2$ is not H when X is N; and Formula (VI) has the structure:

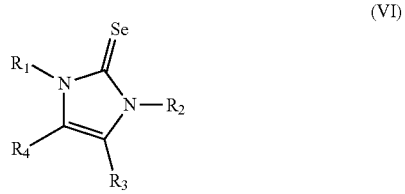

(VI)

wherein $R_1$ and $R_2$ are independently selected from the group consisting of H, substituted or unsubstituted alkyl, substituted or unsubstituted cycloalkyl, substituted or unsubstituted alkenyl, substituted or unsubstituted cycloalkenyl, or substituted or unsubstituted aryl; and wherein $R_3$ and $R_4$ are independently selected from the group consisting of substituted or unsubstituted alkyl, substituted or unsubstituted cycloalkyl, substituted or unsubstituted alkenyl, substituted or unsubstituted cycloalkenyl, or substituted or unsubstituted aryl.

2. The process of claim 1, wherein the metal salt is selected from the group consisting of metal carboxylates, metal phosphonates, and metal halides.

3. The process of claim 2, wherein the metal salt comprises a metal oleate.

4. The process of claim 1, wherein the metal is selected from the group consisting of Pb, Cd, Cu, Zn, In, Ga, Hg, Fe, Mo, and Mn.

5. The process of claim 1, wherein the precursor compound comprises a sulfur compound of Formula (I).

6. The process of claim 5, wherein $R_1$ and $R_2$ of the sulfur compound of Formula (I) comprise entities that are independently selected from the group consisting of unsubstituted alkyl, unsubstituted alkenyl, unsubstituted cycloalkyl, and substituted or unsubstituted aryl.

7. The process of claim 1, wherein the precursor compound comprises N-phenyl-N'-ortho-tolylthiourea.

8. The process of claim 1, wherein the precursor compound comprises N-phenyl-N'-2-ethylhexylthiourea.

9. The process of claim 1, wherein the precursor compound comprises N-n-hexyl-N',N'-di-n-butylthiourea.

10. The process of claim 1, wherein the precursor compound comprises N-phenyl-N'-n-dodecylthiourea.

11. The process of claim 1, wherein the precursor compound comprises N,N-diallyl-N-n-butyl-selenourea.

12. The process of claim 1, wherein the precursor compound comprises a selenium compound of Formula (V).

13. The process of claim 1, wherein the nanocrystals have a median particle size in a range from about 2 nm to about 8 nm.

14. The process of claim 1, wherein the nanocrystals further comprise nanocrystals having a narrow particle size distribution such that the standard deviation (σ) of the particle size distribution is less than or equal to 8% of the median particle size of the nanocrystals.

15. A process for preparing a core-shell nanocrystal, comprising contacting a core nanocrystal in an organic solvent with a mixture comprising a metal salt and a precursor compound selected from the group consisting of sulfur compounds of Formulae (I)-(IV) and selenium compounds of Formulae (V) and (VI) at a temperature in a range of from about 80° C. to about 370° C. to form a suspension of monodispersed core nanocrystals having median particle size and a particle size distribution characterized by a standard deviation, such that the standard deviation (σ) of the particle size distribution is less than or equal to 13% of the median particle size of the core nanocrystals, wherein Formula (I) has the structure:

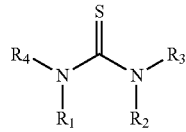

(I)

wherein $R_1$, $R_2$, and $R_3$ are independently selected from the group consisting of H, substituted or unsubstituted alkyl, substituted or unsubstituted cycloalkyl, substituted or unsubstituted alkenyl, substituted or unsubstituted cycloalkenyl, or substituted or unsubstituted aryl;
$R_4$ is independently selected from the group consisting of substituted or unsubstituted alkyl, substituted or unsubstituted cycloalkyl, substituted or unsubstituted alkenyl, substituted or unsubstituted cycloalkenyl, or substituted or unsubstituted aryl;

Formula (II) has the structure:

(II)

wherein $R_1$ and $R_2$ are independently selected from the group consisting of H, substituted or unsubstituted alkyl, substituted or unsubstituted cycloalkyl, substituted or unsubstituted alkenyl, substituted or unsubstituted cycloalkenyl, or substituted or unsubstituted aryl;

Formula (III) has the structure:

(III)

wherein $R_1$ and $R_2$ are independently selected from the group consisting of H, substituted or unsubstituted alkyl, substituted or unsubstituted cycloalkyl, substituted or unsubstituted alkenyl, substituted or unsubstituted cycloalkenyl, or substituted or unsubstituted aryl;

Formula (IV) has the structure:

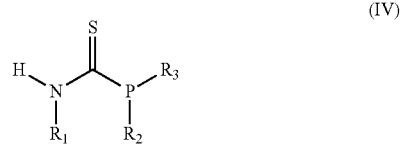

(IV)

wherein $R_1$, $R_2$, and $R_3$ are independently selected from the group consisting of H, substituted or unsubstituted alkyl, substituted or unsubstituted cycloalkyl, substituted or unsubstituted alkenyl, substituted or unsubstituted cycloalkenyl, or substituted or unsubstituted aryl;

Formula (V) has the structure:

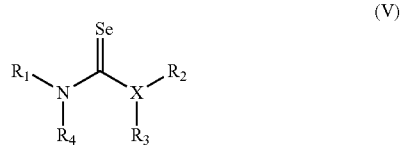

(V)

wherein $R_1$, $R_2$, $R_3$, and $R_4$ are independently selected from the group consisting of H, substituted or unsubstituted alkyl, substituted or unsubstituted alkenyl, substituted or unsubstituted cycloalkyl, substituted or unsubstituted cycloalkenyl, and substituted and unsubstituted aryl; and
X is selected from the group consisting of N, O, S, Se, and P; and wherein $R_2$ is absent when X is O, S, or Se; and wherein $R_2$ is not H when X is N; and Formula (VI) has the structure:

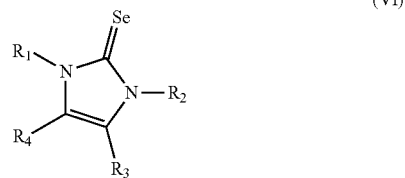

(VI)

wherein $R_1$ and $R_2$ are independently selected from the group consisting of H, substituted or unsubstituted alkyl, substituted or unsubstituted cycloalkyl, substituted or unsubstituted alkenyl, substituted or unsubstituted cycloalkenyl, or substituted or unsubstituted aryl; and wherein $R_3$ and $R_4$ are independently selected from the group consisting of substituted or unsubstituted alkyl, substituted or unsubstituted cycloalkyl, substituted or unsubstituted alkenyl, substituted or unsubstituted cycloalkenyl, or substituted or unsubstituted aryl.

16. The process of claim 15, wherein the core nanocrystal comprises cadmium selenide (CdSe).

17. The process of claim 15, wherein the metal salt is selected from the group consisting of metal carboxylates, metal phosphonates, and metal halides.

18. The process of claim 17, wherein the metal salt comprises a metal oleate.

19. The process of claim 15, wherein the metal is selected from the group consisting of Pb, Cd, Cu, Zn, In, and Ga.

20. The process of claim 19, wherein the metal comprises Cd.

21. The process of claim 15, wherein the precursor compound comprises a sulfur compound of Formula (I).

22. The process of claim 21, wherein $R_1$ and $R_2$ of the sulfur compound of Formula (I) further comprise entities that are independently selected from the group consisting of unsubstituted alkyl, unsubstituted alkenyl, unsubstituted cycloalkyl, and substituted or unsubstituted aryl.

23. The process of claim 21, wherein the precursor compound comprises N-n-hexyl-N',N'-di-n-octylthiourea.

24. The process of claim 21, wherein the precursor compound comprises N,N-diallyl-N-n-butyl-selenourea.

25. The process of claim 1, wherein the nanocrystals have a median particle size of about 5 nm and the standard deviation ($\sigma$) of the particle size distribution is less than or equal to about 0.4 nm.

26. The process of claim 1, wherein the nanocrystals have a median particle size of about 7 nm and the standard deviation ($\sigma$) of the particle size distribution is less than or equal to about 0.6 nm.

27. The process of claim 1, wherein the precursor compound comprises a sulfur compound of Formula (II).

28. The process of claim 1, wherein the precursor compound comprises a sulfur compound of Formula (III).

29. The process of claim 1, wherein the precursor compound comprises a sulfur compound of Formula (IV).

30. The process of claim 1, wherein the precursor compound comprises a selenium compound of Formula (VI).

* * * * *